United States Patent [19]

Kotick et al.

[11] 4,272,541

[45] Jun. 9, 1981

[54] 7,8 AND 7-8 SUBSTITUTED 4,5α-EPOXYMORPHINAN-6-ONE COMPOUNDS, AND METHODS OF TREATING PAIN AND DRUG DEPENDENCE WITH THEM

[75] Inventors: Michael P. Kotick, Elkhart, Ind.; Robert N. Schut, Edwardsburg, Mich.; Joseph O. Polazzi; David L. Leland, both of Elkhart, Ind.

[73] Assignee: Miles Laboratories, Inc., Elkhart, Ind.

[21] Appl. No.: 56,549

[22] Filed: Jul. 11, 1979

Related U.S. Application Data

[63] Continuation-in-part of Ser. No. 911,939, Jun. 2, 1978, abandoned, which is a continuation-in-part of Ser. No. 876,640, Feb. 10, 1978, abandoned.

[51] Int. Cl.³ .................. A61K 31/485; C07D 489/02
[52] U.S. Cl. ........................................ 424/260; 546/45
[58] Field of Search ........................... 546/45; 424/260

[56] References Cited

U.S. PATENT DOCUMENTS

| | | | |
|---|---|---|---|
| 2,178,010 | 10/1939 | Small et al. | 546/45 |
| 2,766,245 | 10/1956 | Gates, Jr. | 546/74 |
| 3,300,500 | 1/1967 | Sawa et al. | 546/74 |
| 4,089,855 | 5/1978 | Chatterjie et al. | 546/45 |
| 4,100,288 | 7/1978 | Merz et al. | 424/260 |
| 4,230,712 | 10/1980 | Kotick et al. | 424/260 |
| 4,232,028 | 11/1980 | Razdan et al. | 424/260 |

OTHER PUBLICATIONS

Bentley, The Chemistry of the Morphine Alkaloids, Oxford, the Clarendon Press (1954), pp. 263-271.
von Braun, et al., Chemische Berichte, vol. 59, pp. 1081-1090 (1926).

*Primary Examiner*—Anton H. Sutto
*Assistant Examiner*—Diana G. Rivers
*Attorney, Agent, or Firm*—Jerome L. Jeffers

[57] ABSTRACT

Disclosed are 7,8 and 7-8 substituted 4,5α-epoxymorphinan-6-one compounds characterized by the structural formula:

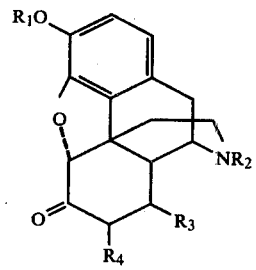

I

In the foregoing formula $R_1$ may be H or methyl, $R_2$ is cyclopropylmethyl, cyclobutylmethyl, allyl or tetrahydrofurfuryl, $R_3$ is H, β-methyl, β-ethyl or α-ethyl and $R_4$ is H or α-methyl. Particular compounds corresponding to the foregoing description are useful as mixed analgesics/narcotic antagonists whereas others have been found to be pure narcotic antagonists.

34 Claims, No Drawings

7,8 AND 7-8 SUBSTITUTED 4,5α-EPOXYMORPHINAN-6-ONE COMPOUNDS, AND METHODS OF TREATING PAIN AND DRUG DEPENDENCE WITH THEM

CROSS-REFERENCE TO RELATED APPLICATIONS

This application is a continuation-in-part of U.S. patent application Ser. No. 911,939 filed June 2, 1978, which is in turn a continuation-in-part of U.S. patent application Ser. No. 876,640, filed Feb. 10, 1978, which applications are now abandoned.

BACKGROUND OF THE INVENTION

1. Field of the Invention

Certain well known narcotic analgesics belong to the class of 4,5α-epoxymorphinan compounds which have the following basic ring system, in which the atoms are numbered as indicated.

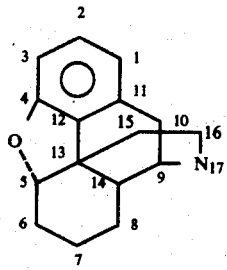

The two most familiar compounds of this class are morphine and its 3-methyl ether, codeine, with the structures indicated below.

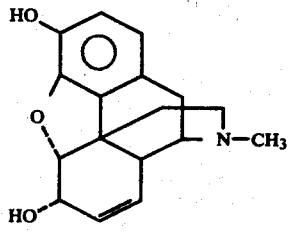

Morphine

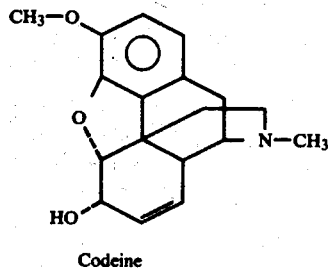

Codeine

When the 6-hydroxyl group of each of these compounds is oxidized to an oxo group, the compounds conveniently are referred to as morphinone and codeinone, respectively. When the N-methyl groups of the latter compounds are replaced by other substituent groups they may be referred to as N-substituted normorphinones and norcodeinones, respectively. There are two types of nomenclature commonly used for describing compounds herein. The trivial names, such as morphine or morphinone, are widely accepted and used for the sake of brevity and clarity. The Chemical Abstracts nomenclature is preferred and is used wherever precision is needed. Table A gives the trivial names and Chemical Abstracts names for commonly referred to compounds herein.

Morphine and its relatives are used primarily for the relief of pain (i.e., as analgesics). They are narcotic and possess dependence-inducing ability and produce other side effects that make them less than ideal analgesics (emesis, constipation, sweating, respiratory depressions, miosis). A compound with the appropriate profile of analgesic (agonist) and narcotic antagonist actions which is not morphine-like has potential as an analgesic agent for treatment of moderate to severe pain without liability of drug dependence. Furthermore, a compound having only strong narcotic antagonist action may be a desirable agent for treatment of drug dependence.

TABLE A

| Trivial Name | NOMENCLATURE Chemical Abstract Name |
|---|---|
| morphine | 7,8-didehydro-4,5α-epoxy-17-methylmorphinan-3,6α-diol. |
| morphinone | 7,8-didehydro-4,5α-epoxy-3-hydroxy-17-methylmorphinan-6-one. |
| normorphinone | 7,8-didehydro-4,5α-epoxy-3-hydroxymorphinan-6-one. |
| dihydromorphine | 4,5α-epoxy-17-methylmorphinan-3,6α-diol. |
| dihydromorphinone | 4,5α-epoxy-3-hydroxy-17-methylmorphinan-6-one. |
| codeine | 7,8-didehydro-4,5α-epoxy-3-methoxy-17-methylmorphinan-6α-ol. |
| norcodeinone | 7,8-didehydro-4,5α-epoxy-3-methoxymorphinan-6-one. |
| dihydrocodeine | 4,5α-epoxy-3-methoxy-17-methylmorphinan-6α-ol. |
| dihydrocodeinone | 4,5α-epoxy-3-methoxy-17-methylmorphinan-6-one. |

2. Prior Art

The only known 4,5α-epoxymorphinan compounds possessing substituents other than a hydrogen atom in the 8-position are those with a halogen, nitrogen or oxygen atom at C-8. Yeh, et al. (J. Pharm. Sci. 6: 902 [1976]) report β-halomorphides, i.e., 6,7-didehydro-4,5α-epoxy-8-halo-17-methylmorphinan-3-ols, which are analgesic compounds. Rapaport and Barber (U.S. Pat. No. 4,054,566; J. Med. Chem. 19: 1175 [1976]) report the preparation of 8-chloro, 8-bromo, and 8-iodocodeinones, used as intermediates in the preparation of codeinone. Seki (Chem. Pharm. Bull. 14: 445 [1966]) has reported various compounds related to codeinone and substituted at the 8-position with a tertiary amine group or a halogen group. Weiss (J. Org. Chem. 12: 1505 [1957]) has reported 8,14-dihydroxy-7,8-dihydromorphinone and the similar codeinone analog. Tada et al. (Tet. Let. [22], 1805 [1969] have reported 8-hydroxyethoxy-14-hydroxycodeinone and the similar 8-methoxyethoxy analog.

Compounds having a hydrogen atom at the 8-position have also been reported. Dihydrocodeine, dihydrocodeinone, dihydromorphine and dihydromorphinone have long been known (Merck Index, 9th ed., No. 3148, 4672, 3155, 4700). Gates and Montzka (J. Med. Chem., 7: 127 [1964]) have synthesized 7,8-dihydro-17-cyclopropylmethylnorcodeinone, and 7,8-dihydro-17-cyclopropylmethylnormorphinone; the latter compound had narcotic antagonist activity. Telford et al. (J. Pharmacol. Exp. Therap. 133: 106 [1961]; hereafter "TELFORD") reported 7,8-dihydro-N-allylnorcodeinone (17-allyl-4,5α-epoxy-3-methoxymorphinan-6-one) and disclosed that it had weak analgesic properties.

Additional references which discuss structure-activity relationships in general are: Archer and Harris (Progr. in Drug Research 8: 261 [1965]); Lewis, Bentley and Cowan (Ann. Rev. Pharmacol. 11: 241 [1971]); Kosterlitz and Waterfield (Ann. Rev. Pharmacol. 15: 29 [1975]); and Merz et al. (J. Med. Chem. 20: 844 [1977]).

Small et al disclose in U.S. Pat. No. 2,178,010 (issued Oct. 31, 1939) the reaction of dihydrothebaine:

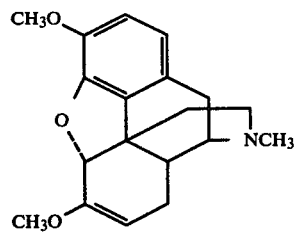

with methylmagnesium iodide in refluxing ether solution for 108 hours to give, after workup which includes acid hydrolysis, a mixture from which may be isolated in 45–58% crude yield (15–17.5% recrystallized) methyldihydrothebainone:

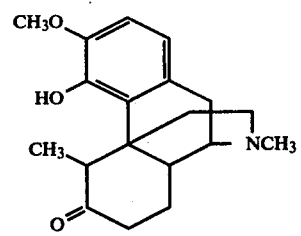

and a 9–11% yield (5–6% recrystallized) of isomethyldihydrothebainone:

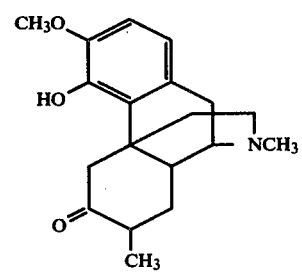

Small et al. also report in J. Org. Chem., 3, 204 (1938) the reaction of dihydrocodeinone enol acetate:

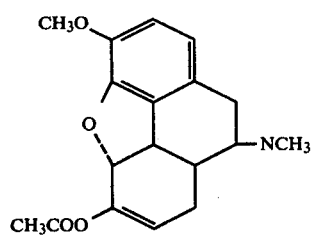

with methylmagnesium iodide for 24 hours in boiling ether to give a 74% yield of V and some VI with no mention of its exact percent yield. It should be noted that the 7-methyl compound VI is the minor product of these reactions and is difficult to obtain.

The introduction of a 7-ketone into the morphinane nucleus with concurrent cleavage of the 4,5-epoxy bond has been reported by Rearick and Gates in Tetrahedron Letters, 507 (1970). They report that treatment of 14-bromocodeinone:

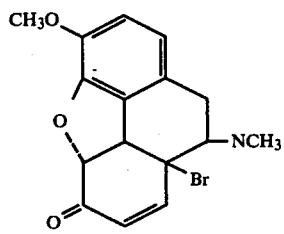

with Claisens alkali gives the 7-keto morphinane IX:

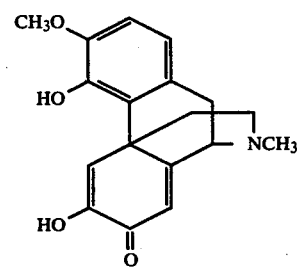

Sawa et al report the preparation of desoxysinomenine characterized by the formula:

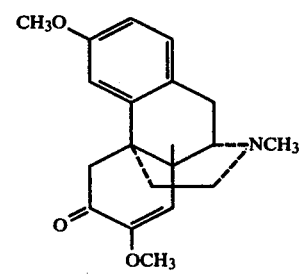

and desoxydihydrosinomenine characterized by the formula:

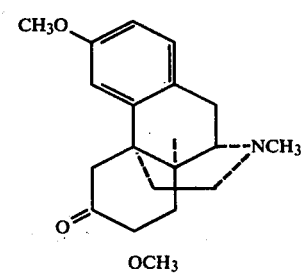

in Tetrahedron, 15, 144 (1961) from the naturally occuring alkaloid, sinomenine:

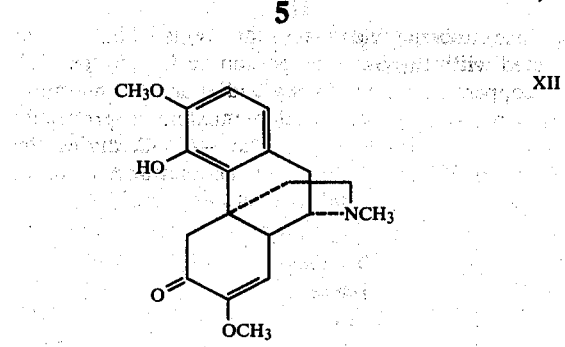

Introduction of 7-substituents on the 4,5-epoxy morphinane nucleus, without cleavage of the epoxy bond has been reported by several workers. Bentley et al report in Chem. Comm., JCS C, 57 (1969) that nitrosyl chloride reacts with thebaine in methanol to give the dimethyl ketal of 7-hydroxyiminoneopinone. Reaction of thebaine with iodine in the presence of $AgNO_2$ in methanol-chloroform likewise gives the dimethyl ketal of 7β-iodoneopinone.

Lester et al report in Tetrahedron, 20, 1407 (1964) and 21, 771 (1965) that 14-hydroxy-dihydrocodeinone may be converted to the 7-hydroxyimino derivative by reaction with amylnitrite in chloroform containing ethanolic HCl. This compound can be converted to an ethylene ketal and hydrolyzed to the 7-keto-6-ketal which upon further reaction with dimethylsulphoxonium methylide gives the oxirane.

SUMMARY OF THE INVENTION

The present invention involves 7,8 and 7-8 substituted 4,5α-epoxymorphinan-6-one compounds characterized by the structural formula:

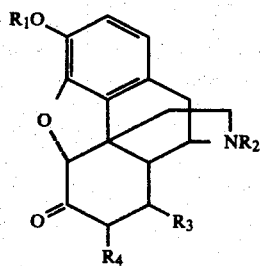

wherein $R_1$ is H or methyl; $R_2$ is cyclopropylmethyl, cyclobutylmethyl, allyl or tetrahydrofurfuryl; $R_3$ is H, β-methyl, β-ethyl or α-ethyl and $R_4$ is H or α-methyl provided that:

i. when $R_2$ is allyl, $R_3$ is β-ethyl, $R_4$ is H and $R_1$ is H;

ii. when $R_2$ is tetrahydrofurfuryl, $R_3$ is β-ethyl, $R_4$ is H and $R_1$ is H;

iii. when $R_2$ is cyclobutylmethyl, $R_1$ is H and $R_3$ and $R_4$ are, respectively, either β-ethyl and H, β-methyl and α-methyl or β-methyl and H;

iv. when $R_2$ is cyclopropylmethyl and $R_1$ is methyl $R_3$ is β-ethyl and $R_4$ is H; and v. when $R_2$ is cyclopropylmethyl and $R_1$ is H, $R_3$ and $R_4$ are, respectively, either β-ethyl and H, H and α-methyl, α-ethyl and H or β-methyl and α-methyl.

DETAILED DESCRIPTION AND PREFERRED EMBODIMENTS

Formula I', below, characterizes those compounds of the present invention in which the novel feature is alkyl substitution at the 8-position:

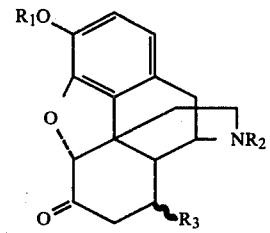

Formula I', by use of a serpentine line (⌇) denotes orientation of the covalent bond attaching $R_3$ to the rest of the molecule as being either above or below the plane of reference. When the group projects below the plane of reference it is referred to as being in the α-position and such orientation is represented by a dashed (---) line. When the group projects above the plane of reference it is referred to as being in the β-position and is represented by a wedged (◂) line. We have found that those compounds corresponding to Formula I' in which $R_3$ is in the β-configuration possess desirable pharmacological properties, and it has been discovered that a particular compound in which $R_3$ is in the α-configuration, 17-cyclopropylmethyl-4,5α-epoxy-8α-ethyl-3-hydroxymorphinan-6-one hydrochloride (TR-5436), is a strong analgesic which also exhibits narcotic antagonist activity.

The following description of the process used to prepare compounds of Formula I' describes $R_3$ as being in the β-configuration. This is the case because the 8β isomer is the major product of this reaction. However, the 8α-alkyl compound is coproduced in an amount of about 2-8% of the total product; we isolated, by chromatography, sufficient 8α-ethyldihydrocodinone to allow preparation of the corresponding potential mixed agonists/antagonists.

Compounds of Formula I' are synthesized by reaction of a first starting material, codeinone, Formula XIII, a known compound prepared from thebaine by the procedure of Gavard et al. (Bull. Soc. Chim. Fr., 486 [1965]),

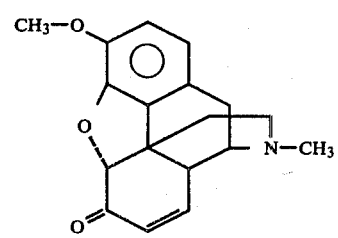

with a lithium lower alkyl copper reagent selected from the class consisting of lithium diethyl copper and lithium dimethyl copper, via a conjugate 1,4-addition reaction. The use of lithium lower dialkyl copper reagents in 1,4-addition processes has been described by Posner (Org. Reactions 19:1 [1972]). Posner, however, does not teach the use of such reactions in the codeinone or any other 4,5α-epoxymorphinan system.

The lithium lower dialkyl copper reagent is prepared by the addition of a solution containing about 2 molar equivalents of ethyl or methyl lithium to a stirred suspension containing about 1 molar equivalent of copper iodide, in a solvent such as ether, tetrahydrofuran, or the like, under a moisture-free atmosphere of nitrogen or argon. Lithium diethyl copper is prepared at −78° C. and allowed to warm to −40° C. Lithium dimethyl copper is prepared at 0° C.

A solution of codeinone in a halogenated hydrocarbon solvent, such as methylene chloride, ethylene chloride, dichloroethane and the like, preferably methylene chloride, or an aromatic hydrocarbon solvent, such as benzene, toluene, xylene and the like is added to and reacted with the stirred suspension of the lithium lower dialkyl copper reagent preferably under an inert, moisture-free atmosphere. The reaction mixture is preferably maintained at about −78° C. to +10° C., most preferably about −40° C. to 0° C., during the period of addition of the codeinone solution and during the reaction period of up to about 10 minutes. The molar ratio of codeinone to lithium lower dialkyl copper reagent preferably ranges from about 1:1 to 1:3, respectively.

The reaction mixture, preferably warmed to about 0° C., is then quenched with an aqueous solution of an ammonium compound, such as ammonium chloride, ammonium hydroxide or the like, preferably in an amount in molar excess of the copper contained in the reaction mixture, and the resulting mixture is stirred for up to 1 hour to produce an 8β-lower alkyl codeinone product having the structural Formula XIV,

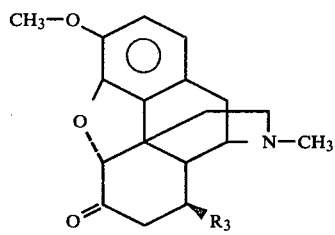

XIV wherein $R_3$ is ethyl or methyl.

The aqueous phase of the above mixture is separated and adjusted to approximately pH 12 by addition of a strong base, such as 50% sodium or potassium hydroxide. Then, the basic aqueous solution is extracted with an organic solvent, such as ether, chloroform or the like. The organic phase is washed, dried, and evaporated to isolate the product having structural Formula XIV.

An alternate method for the preparation of the 8β-ethyl codeinone of Formula XIV involves the preparation of 8β-vinyl codeinone, which is then hydrogenated.

8β-Vinyl codeinone is synthesized by reaction of codeinone, having Formula XIII above, with lithium divinyl copper, via a conjugate 1,4-addition reaction. The lithium divinyl copper reagent is prepared by the addition of a solution containing 2 molar equivalents of vinyl lithium to a stirred suspension containing 1 molar equivalent of copper iodide, in a solvent such as ether, tetrahydrofuran or the like, under a moisture-free atmosphere such as nitrogen or argon at about −78° C.

A solution of codeinone in a halogenated hydrocarbon solvent, such as methylene chloride, ethylene chloride, dichloroethane and the like, preferably methylene chloride, or in an aromatic hydrocarbon solvent such as benzene, toluene, xylene and the like, is added to and reacted with the stirred suspension of the lithium divinyl copper reagent preferably under an inert moisture-free atmosphere. The reaction mixture is preferably maintained at about −78° C. to −40° C. during the period of addition of the codeinone solution and during a reaction period of up to about one hour. The molar ratio of codeinone to lithium divinyl copper reagent preferably ranges from about 1:1 to 1:3, respectively.

The reaction mixture is then quenched, preferably after allowing it to warm to about 0° C., with an aqueous solution of an ammonium compound, such as ammonium chloride, ammonium hydroxide or the like, preferably in an amount in molar excess of the copper contained in the reaction mixture, and the resulting mixture is stirred for up to one hour to produce 8β-vinyl codeinone, which is isolated as described above for the isolation of compound having Formula XIV.

The 8β-vinylcodeinone is then dissolved in a suitable organic solvent such as ethyl acetate, ethanol, acetone or the like and reacted with hydrogen in the presence of a catalyst such as Palladium on carbon, Rhodium on carbon, Platinum on carbon and the like under acidic conditions. The hydrogen pressure is preferably maintained at about 50 psi during the reaction for a sufficient period of time usually from about one to four hours; to complete the hydrogenation. The acidic condition can be achieved by the addition of a suitable mineral acid such as hydrochloric acid, nitric acid, sulfuric acid and the like. After filtration and removal of the solvent, the 8β-ethyl codeinone is isolated as the hydrochloride salt.

The product having Formula XIV is dissolved in a suitable organic solvent such as ether, chloroform or the like, preferably containing a suitable acid acceptor, such as anhydrous potassium carbonate or sodium carbonate or the like. A solution of a cyanogen halide, such as cyanogen bromide, cyanogen chloride or cyanogen iodide, is then added with stirring over a period up to about 30 minutes. The suspension is preferably stirred at a temperature from about 20° C. up to the reflux temperature of the solvent for up to 2 hours, to produce an 8β-lower alkyl-17-cyanonorcodeinone product having the structural Formula XV:

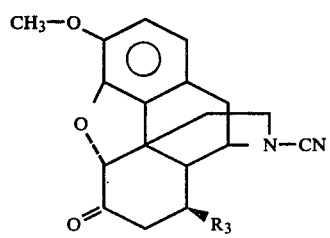

XV wherein $R_3$ is as above.

After cooling the suspension to a temperature sufficient to facilitate removal of insoluble material, the insoluble material is removed by filtration or centrifugation, and the solvent is evaporated to isolate the 8β-lower alkyl-17-cyanonorcodeinone product having Formula XV.

The 8β-lower alkyl-17-cyano-norcodeinone product of Formula XV is then hydrolyzed by suspending it in a mineral acid, such as hydrochloric, sulfuric, nitric and the like, preferably about 1 to 6 N, and preferably heating the suspension at reflux temperature for up to about 5 hours, to produce an 8β-lower alkyl-norcodeinone product having the structural Formula XVI,

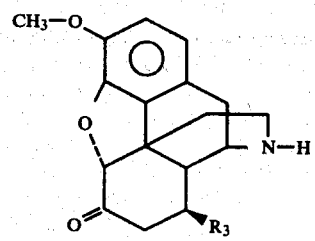

wherein R₃ is as above, which is isolated as the acid addition salt by evaporation of the solvent.

The 8β-lower alkyl norcodeinone product of Formula XVI, or optionally its acid addition salt, is then reacted with an alkylating agent such as allyl bromide, cyclopropylmethyl bromide, cyclobutylmethyl bromide, tetrahydrofurfuryl bromide or tetrahydrofurfuryl camphor-10-sulfonate in the presence of an acid acceptor, such as the carbonate or bicarbonate salts of potassium or sodium. The molar ratios of the 8β-lower alkyl-norcodeinone product of Formula XVI to alkylating agent to acid acceptor preferably range from 1:1:2 to 1:2:4 respectively. The reaction is carried out in a suitable polar organic solvent, such as dimethylformamide, dimethylsulfoxide, ethanol and the like, preferably under an inert, moisture-free atmosphere of nitrogen or argon at a temperature of from about 50° C. to about 110° C. Dimethylformamide (DMF) is the preferred solvent. The resulting product having Formula I', where R₁ is methyl, is then isolated by procedures standard to the art, such as solvent extraction or chromatography.

Compounds having Formula I', where R₁ is hydrogen, are prepared by 0-demethylating the compound of Formula I', where R₁ is methyl, by use of a hydrolytic reagent, such as pyridine hydrochloride, hydrobromic acid, preferably concentrated (48%) hydrobromic acid, or the like. We prefer to use pyridine hydrochloride at a temperature of from 180° C.-200° C. for 1 to 2 hours.

When it is desired to have a product with increased water solubility, the organic or inorganic acid addition salts of compounds having Formula I can be prepared. Examples of pharmaceutically acceptable acid addition salts are the tartrate, hydrochloride, hydrobromide, maleate or the like. We prefer the hydrochloride salt. The hydrochloride salt is preferably obtained by dissolving the free base in an organic solvent, such as ether or ethyl acetate, and adding gaseous hydrogen chloride or is obtained by dissolving the free base in a lower alcohol, adding aqueous hydrochloric acid and evaporating the solvents. Crystallization of the hydrochloride salts can be achieved with a variety of solvents, for example, a lower alcohol such as methanol, ethanol or isopropanol or the like by the addition of a lower ester, such as methyl acetate, ethyl acetate, or isopropyl acetate or the like, followed by removal of the alcohol by boiling.

The following examples are provided to further illustrate the inventive concept described above and are not intended to limit the invention.

EXAMPLE 1

This Example illustrates the preparation of 17-cyclopropylmethyl-4,5α-epoxy-8β-ethyl-3-methoxymorphinan-6-one hydrochloride (TR 5109) and also describes the preparation of intermediates to the title product.

A. 4,5α-Epoxy-8β-ethyl-3-methoxy-17-methylmorphinan-6-one (TR-5059)

I. Preparation of Ether-Benzene.

Ethyl lithium was prepared under argon by the dropwise addition of ethyl chloride (11.1 g, 172 mmoles) in 50 ml of ether to a suspension of finely dispersed lithium (345 mmole, 2.4 g) in 100 ml of ether followed by stirring at 0° C. for 20 minutes. After cooling to −78° C., the ethyl lithium suspension was transferred by use of argon pressure to a suspension of CuI (16.0 g, 84 mmole) in 800 ml ether with stirring at −78° C. The resultant suspension was allowed to warm to −40° C. and a warm solution of codeinone (20.0 g, 67 mmole; prepared by the method of Gavard et al. (Bull. Soc. Chim. Fr., 486 [1965]) in 400 ml dry benzene was added at a rate to keep the temperature at about −40° C. After stirring at −40° C. for 10 minutes, the mixture was allowed to warm to 0° C. The mixture was then poured into saturated NH₄Cl solution (500 ml) and stirred rapidly for about 1 hour. The phases were separated, and the aqueous phase was adjusted to about pH 12 by the addition of 50% NaOH solution. The basic aqueous phase was then extracted with three portions of chloroform, and the combined organic phases were back-washed with saturated NH₄Cl solution, dried over MgSO₄, and evaporated to yield a crystalline residue. The residue was crystallized from ethyl acetate to give TR 5059, 12.2 g (55%), mp 146.5°-148° C. Additional product (3.95 g) was obtained from the mother liquor. Recrystallization from ethanol gave pure TR-5059, mp 147°-148° C. NMR (CDCl₃); δ6.70, s, 2H (aromatic); 4.70, s, 2H (H5); 3.93, s, 3H (CH₃O—), 2.46, s, 3H (CH₃N—), 1.03–0.73, unsymmetrical t, 3H (CH₃CH₂—).

The HCl salt of TR 5059 was prepared by dissolving the free base in ethanol, adding an excess of concentrated HCl and evaporating to dryness. The residue was azeotroped with ethanol; 1:1 V/V ethanol:benzene, then benzene, and crystallized from ethanol-ethyl acetate to give analytically pure TR-5059.HCl, mp 285°-288° C.

Anal. Calcd. for C₂₀H₂₅NO₃.HCl: C, 66.02; H, 7.20; N, 3.85; Cl, 9.74. Found: C, 65.82; H, 7.04; N, 3.79; Cl, 9.87.

II. Preparation of Ether-Methylene Chloride

Ethyl lithium was prepared from lithium (0.9 g) in ether (30 ml) by the addition of ethyl chloride (5.0 ml) in ether (20 ml) and added to CuI (6.0 g) in ether (100 ml) at −78° C. as described in part I above. The suspension was warmed to −40° C. and a solution of codeinone (5.0 g) in methylene chloride (100 ml) added rapidly dropwise. The reaction mixture was treated as above and TR 5059 (5.3 g, 96%) was isolated as a foam whose spectral characteristics were identical to the product as prepared in Part I, above.

III. Preparation using a lithium divinyl copper reagent (a) 4,5α-Epoxy-3-methoxy-17-methyl-8β-vinylmorphinan-6-one (TR-5106)

Vinyl lithium was prepared at −78° C. under argon in 60 ml of ether by stirring vinyl bromide (4.5 g, 42 mmol) and t-butyl lithium (84 mmole, 52.5 ml of a 1.6 M solution in pentane) for one hour. The resulting suspension was added to a stirred suspension of CuI (4.00 g, 21 mmole) in 200 ml of ether at $-78°$ C. under argon. Codeinone (5.00 g, 16.8 mmole) was added as in Example 1 and the mixture slowly allowed to warm to $-5°$ C. before being poured into NH$_4$Cl solution. Further processing as described in Example 1 gave 5.4 g of a syrup which was chromatographed over Silica Gel G (500 g) using 15:1 V/V chloroform:methanol as the eluent. Fractions containing the desired product were pooled and evaporated to give 3.00 g (55%) of TR 5106 as white crystals, mp 132°-134° C. NMR (CDCl$_3$): δ6.70, s, 2H (aromatic); 4.70, s, 1H (H5); 5.8-5.4, 1H, m (—CH=CH$_2$); 5.1-4.8, 2H, m (—CH=CH$_2$); 3.93, s (CH$_3$O—); 2.43, s (CH$_3$N—).

The HCl salt was prepared as in Example 1 and recrystallized from ethanol to give pure TR-5106.HCl, mp 276°-278° C. dec.

Anal. Calcd. for C$_{20}$H$_{23}$NO$_3$.HCl: C, 66.38; H, 6.68; N, 3.87. Found: C, 66.11; H, 6.65; N, 3.82.

(b) 4,5α-Epoxy-8β-ethyl-3-methoxy-17-methylmorphinan-6-one

To a solution of 4,5α-epoxy-3-methoxy-17-methyl-8β-vinylmorphinan-6-one (9.0 g) in 95% ethanol was added 2 ml of concentrated hydrochloric acid followed by 10% palladium/charcoal (1.0 g.). The mixture was hydrogenated at an initial pressure of 50 psi for 2.5 hours. The reaction mixture was filtered, the filtrate made acidic by the addition of hydrochloric acid and evaporated to a crystalline solid. The solid was recrystallized from ethyl acetate with the addition of ethanol to give, after drying, 8.7 g (90%) of the 8-ethyl product TR-5059.HCl, mp 285°-288° C.

B. 17-Cyano-4,5α-epoxy-8β-ethyl-3-methoxymorphinan-6-one 4,5α-Epoxy-8β-ethyl-3-methoxy-17-methylmorphinan-6one (5.00 g, 13.7 mmole; prepared in Part A) was dissolved in 50 ml chloroform. After the addition of K$_2$CO$_3$ (2.84 g, 20.6 mmole), the stirred suspension was treated dropwise with a solution of cyanogen bromide (1.95 g, 18.4 mmole) in 40 ml chloroform. The mixture was stirred at room temperature for 30 minutes and heated for 1.5 hours at reflux temperature. After cooling, the insoluble material was removed from the mixture by filtration and the filtrate was evaporated to a crystalline residue which was boiled with ethanol (30 ml). After chilling, the crystals were collected to give 4.30 g (92%) of white needles, mp sinters 194° C., melts 197°-198.5° C.

C. 4,5α-Epoxy-8β-ethyl-3-methoxymorphinan-6-one hydrochloride

A suspension of 17-cyano-4,5α-epoxy-8β-ethyl-3-methoxymorphinan-6-one (4.30 g; prepared in Part B) in 100 ml 2 N HCl was refluxed for 4 hours. The solution was evaporated to a crystalline residue which was suspended in ethanol. After cooling, the crystals were collected and dried to give 3.95 g (89%) of product, mp. decomposes slowly above 260° C.

D. 17-Cyclopropylmethyl-4,5α-epoxy-8β-ethyl-3-methoxymorphinan-6-one Hydrochloride (TR-5109)

A mixture of 4,5α-epoxy-8β-ethyl-3-methoxymorphinan-6-one hydrochloride (2.30 g, 6.6 mmole; prepared in Part C), NaHCO$_3$ (1.22 g, 14.5 mmole) and cyclopropylmethyl bromide (1.33 g, 9.9 mmole; prepared according to Neth. Appl. 6,613,986; Chem. Abst. 68: 59608 m [1968]) in 30 ml DMF was heated in an oil bath at 100° C. for 16 hours under an argon atmosphere. The cooled suspension was filtered, and the filtrate was evaporated to yield a semi-solid residue. The residue was partitioned between dilute ammonia and chloroform. The aqueous phase was extracted with two additional portions of chloroform. The combined organic phases were dried, filtered and evaporated to give 2.52 g of a syrup. Chromatography of the syrup on Silica Gel G (200 g, 15:1 V/V chloroform:methanol) gave 1.68 g of TR-5109 as the free base which was converted to the HCl salt as in Part A and crystallized from ethyl acetate to give pure TR-5109, mp 207°-209° C.

Anal. Calcd. for C$_{23}$H$_{29}$NO$_3$.HCl: C, 68.39; H, 7.49; N, 3.47. Found: C, 68.05; H, 7.33; N, 3.26.

EXAMPLE 2

17-Cyclopropylmethyl-4,5α-epoxy-8β-ethyl-3-hydroxymorphinan-6-one (TR-5126).

A mixture of TR-5109 (1.0 g; prepared in Example 1) and pyridine hydrochloride (3.0 g) was heated at 200° C. for 2 hours. To isolate the product, the mixture was cooled, diluted with water and made basic by the addition of concentrated ammonium hydroxide. This mixture was then extracted with several portions of methylene chloride, the organic phase was dried and evaporated to give a brown foam (900 mg) which was twice chromatographed over Silica Gel G to give the purified material. Pure fractions containing the desired material was evaporated to give a foam. A sample of the free base of TR-5126 prepared in another reaction, was converted to the hemi-tartate salt by adding an ethanol solution of 1.0 equivalent of d-tartaric acid to a solution of the free base of TR-5126 in ethanol. The crystals which formed were collected and recrystallized twice from agreous ethanol to give pure TR-5126 as the hemi-tartarte salt, mp 248°-250°.

Anal. Calcd for C$_{22}$H$_{27}$NO$_3$.0.5 C$_4$H$_6$O$_6$: C, 67.27; H, 7.06; H, 3.27. Found: C, 66.87; H, 7.31; N, 3.56.

EXAMPLE 3

17-Cyclobutylmethyl-4,5α-epoxy-8β-ethyl-3-hydroxymorphinan-6-one Hydrochloride (TR-5115)

Part A below describes the preparation of an intermediate to the title compound.

A. 17-Cyclobutylmethyl-4,5α-epoxy-8β-ethyl-3-methoxymorphinan-6-one Hydrochloride (TR-5114)

A mixture of 4,5α-epoxy-8β-ethyl-3-methoxymorphinan-6-one hydrochloride (3.00 g, 8.6 mmole; prepared in Example 1C), NaHCO$_3$ (1.59 g, 18.9 mmole) and cyclobutylmethyl bromide (1.92 g, 12.9 mmole; prepared according to Neth. Appl. 6,613,986; Chem Abst. 68: 59608 m [1968]) in 40 ml DMF was heated under argon at 100° C. for 16 hours. Treatment of the reaction mixture as in Example 1D give a syrup (3.00 g) using 15:1 V/V chloroform:methanol as the solvent. Pure fractions were combined to give 2.13 g (65%) of TR-5114. The HCl salt was prepared as in Example 1A and was crystallized from ethyl acetate to give 1.44 g of TR-5114 HCl as white needles, mp 174°–175.5° C.

Anal. Calcd. for $C_{24}H_{33}NO_3 \cdot HCl$: C, 68.97; H, 7.72; N, 3.35; Cl, 8.48. Found: C, 67.59; H, 7.89; N, 3.27; Cl, 8.73.

B.
17-Cyclobutylmethyl-4,5α-epoxy-8β-ethyl-3-hydroxymorphinan-6-one (TR-5115).

A solution of TR-5114·HCl (1.30 g; prepared in Part A) in 10 ml 48% HBr was refluxed for 15 minutes, cooled, diluted with water, and made basic with $NH_4OH$. The resulting suspension was diluted with ethanol and extracted with six portions of methylene chloride. The organic extracts were dried and evaporated to give 1.18 g of a foam which was chromatographed (100 g Silica Gel G, 15:1 V/V chloroform:methanol) to give 630 mg of pure material as a foam. The foam was dissolved in ethanol, excess concentrated HCl was added and the mixture was evaporated to dryness. Azeotropic distillation with an ethanol-benzene mixture followed by azeotropic distillation with benzene gave crystals which were suspended in ethyl acetate and collected to give TR-5115·HCl, 476 mg, mp dec. above 198° C. Recrystallization from water gave pure TR-5115·HCl, mp dec. above 200° C.

Anal. Calcd. for $C_{23}H_{29}NO_3 \cdot HCl$: C, 68.39; H, 7.49; N, 3.57; Cl, 8.78. Found: C, 68.26; H, 7.65; N, 3.47; Cl, 9.12.

EXAMPLE 4
4,5α-Epoxy-8β-ethyl-3-hydroxy-17-tetrahydrofurfuryl-morphinan-6-one Hydrochloride (TR-5271)

Part A describes the preparation of an intermediate to the title compound.

A.
4,5α-Epoxy-8β-ethyl-3-methoxy-17-tetrahydrofurfurylmorphianan-6-one Hydrochloride (TR-5263)

A mixture of 4,5α-epoxy-8β-ethyl-3-methoxymrophinan-6-one hydrochloride (1.00 g, 28.6 mmole; prepared in Example 1C), Syrupy tetrahydrofurfuryl (R/S)-camphor-10-sulfonate (1.36 g, 42.9 mmole; prepared as described by Merz et al., J. Med. Chem. 20: 844 [1977], sodium iodide (0.51 g, 34.3 mmole) and sodium bicarbonate (0.48 g, 57.2 mmole) in 30 ml DMF was heated at 100° C. under an argon atmosphere for 18 hours. The suspension was cooled and filtered, and the filtrate was evaporated to yield a simi-solid residue. The residue was partitioned between dilute ammonia solution and toluene. The aqueous phase was extracted with two additional portions of toluene and the combined orginic phases were dried, filtered, and evaporated to give 1.07 g of a syrup. Chromatography of the syrup (Silic Gel G, 15:1 V/V chloroform:methanol) gave 0.74 g of the desired material, which was converted to the hydrochloride salt as in Example 1A and crystallized from ethyl acetate to give 0.623 g of TR-5263 mp 185.5°–189° C. Recrystallization from methanol-ethyl acetate gave 0.49 g of pure TR-5263, mp dec. 190°–210° C.

Anal. Calcd, for $C_{24}H_{31}NO_4 \cdot HCl$: C, 66.42; H, 7.43; N, 3.23. Found: C, 65.53; H, 7.55; N, 3.24.

B.
4,5α-Epoxy-8β-ethyl-3-hydroxy-17-tetrahydrofurfuryl-morphinan-6-one Hydrochloride (TR-5271)

A mixture of impure TR-5263 (2.40 g; prepared in Part A) and 8.00 g of pyridine hydrochloride was heated at 190°–200° C. for 1 hour. Treatment of the reaction mixture as in Example 2 gave a foam which was purified by chromatography. The product was obtained as a foam which was converted to the HCl salt, also obtained as a foam.

Anal. Calcd. for $C_{23}H_{29}NO_4 \cdot HCl$: C, 65.78; H, 7.20; N, 3.34. Found: C, 64.06; H, 6.92; N, 3.63.

EXAMPLE 5
17-Allyl-4,5α-epoxy-8β-ethyl-3-methoxymorphinan-6-one Hydrochloride (TR-5256)

To a sample of 4,5α-epoxy-8β-ethyl-3-methoxymorphinan-6-one hydrochloride (3.49 g, 10 mmole; prepared in Example 1C) and sodium bicarbonate (15 mmole) in 50 ml dimethylformamide there was added allyl bromide (1 ml, 11 mmole) and the mixture was stirred under argon at about 100° C. for about 16 hours. The solids were removed by filtration and the filtrate was evaporated to a residue under vacuum. The residue was then partitioned between toluene and water. The product (2.97 g) crystallized upon evaporation of the toluene. The hydrochloride salt was prepared as in Example 1A and was crystallized from methanol-ethyl acetate to yield 2.4 g (62%), mp 230°–232° C.

Anal. Calcd. for $C_{22}H_{27}NO_3 \cdot HCl$: C, 67.76; H, 7.25; N, 3.59. Found: C, 67.63; H, 7.17; N, 3.47.

EXAMPLE 6
17-Allyl-4,5α-epoxy-8β-ethyl-3-hydroxymorphinan-6-one Hydrochloride (TR-5266)

A sample of TR-5256 (1.5 g, prepared in Example 5) and 6.0 g of pyridine hydrochloride was heated at 185°–200° C. for about 1 hour. After cooling, the product was isolated as described in Example 2 to yield 986 mg of syrup which was then chromatographed on 100 g of Silica Gel G using 10:1 V/V chloroform:methanol. The purified product (780 mg) was converted to the hydrochloride salt as in Example 1A, yield 228 mg, mp 263° C. dec.

Anal. Calcd. for $C_{21}H_{25}NO_3 \cdot HCl$: C, 67.10; H, 6.97; N, 3.73. Found: C, 66.40; H, 7.03; N, 3.61.

EXAMPLE 7

This example describes the preparation of 17-cyclobutylmethyl-4,5α-epoxy-3-hydroxy-8β-methyl-morphinan-6-one and its intermediates.

A. 8β,17-Dimethyl-4,5α-epoxymorphinan-6-one (Compound 7A)

A solution of dimethyl copper lithium was prepared at 0° under an argon atmosphere by adding methyl lithium (0.210 mole, 126 ml of a 1.8 M solution in ether; available from Alfa Chem. Co.) to a suspension of CuI (20.0 g, 0.105 mole) in 400 ml of anhydrous ether. To this was added in a thin stream a warm solution of codeinone (25.0 g, 0.084 mole; prepared by the method of Gavard et al. Bull. Soc. Chim. Fr., 486 (1965)) in 500 ml of dry benzene and the resulting yellow suspension was stirred at 0° for about 1 hr. The mixture was then poured into 500 ml of saturated $NH_4Cl$ solution and stirred at about 20° C. for about 1 hr. The organic phase was separated from the mixture and the aqueous phase adjusted to about pH 12 by the addition of 50% NaOH solution. The resulting aqueous phase was extracted with three portions of chloroform, and the combined organic phases were backwashed with saturated NH$_4$Cl solution, dried over MgSO$_4$, and evaporated to give a crystalline residue. The resulting residue was dissolved in a minimal amount of hot ethanol and stored at about 4° C. overnight. Tan crystals were collected and dried to give 9.3 g of product. An additional 1.2 g of product were obtained from the mother liquor to give an overall yield of 40%. Analytically pure Compound 7A mp 178°–179.5°, was prepared by recrystallization from ethanol. Nmr (CDCl$_3$): δ6.68, s, 2H (aromatic); 4.65, s, 1H (H5); 3.57, s, 3H (CH$_3$O—); 2.45, s, 3H (CH$_3$N—); 1.02, unsymmetrical doublet, 3H, J=6 Hz (8βCH$_3$—). Ir (CDCl$_3$): 1730 cm$^{-1}$ (saturated C=0). Mass spectrum. m/e 313 (P); 298 (P—CH$_3$).

Anal. Calcd. for C$_{19}$H$_{23}$NO$_3$: C, 72.82; H, 7.40; N, 4.47. Found: C, 72.70; H, 7.59; N, 4.46.

The hydrochloride of Compound 7A prepared by the method described in Example 1A was crystallized from ethanol-ethyl acetate to give Compound 7A.HCl, mp 274°–276°.

Anal. Calcd. for C$_{19}$H$_{23}$NO$_3$.HCl: C, 65.23; H, 6.91; N, 4.00; Cl, 10.13. Found: C, 65.17; H, 6.96; N, 4.05; Cl 10.19.

B.
17-Cyano-4,5α-epoxy-3-methoxy-8β-methyl-morphinan -6-one (Compound 7B)

To a suspension of Compound 7A (9.39 g, 30 mmole; prepared in Example 7A) and powdered anhydrous K$_2$CO$_3$ (6.00 g, 47 mmole) in 60 ml of chloroform was added a solution of cyanogen bromide in chloroform (1.2 eq, 1.0 g/20 ml) dropwise. Stirring was continued for 30 min at about 20° C. after which the mixture was refluxed for 2 hr. After cooling the mixture, the insoluble material therein was removed by filtration. The filtrate was evaporated to a syrup which crystallized upon azeotropic distillation with ethanol. The crystals were boiled with 40 ml of ethanol and collected after storage at 5° C. overnight to give 7.93 g (82% yield) of product, mp 237°–241°.

C. 4,5α-Epoxy-3-methoxy-8β-methylmorphinan-6-one Hydrochloride (Compound 7C)

A mixture of 7.9 g of Compound 7 B (prepared in Example 7B) and 2 N HCl (200 ml) was heated at reflux for about 5 hr. Evaporation of the solvent gave a crystalline residue which was triturated with ethanol. The crystals were collected and air dried to give 8.05 g (98%) of product. Recrystallization from ethanol gave Compound 7C.HCl 297°–300° C. dec.

Anal. Calcd. for C$_{18}$H$_{21}$NO$_3$.HCl: C, 64.38; H, 6.60; N, 4.17; Cl, 10.56. Found: C, 64.64; H, 7.00; N, 4.05; Cl, 10.90.

D.
17-Cyclobutylmethyl-4,5α-epoxy-3-methoxy-8β-methylmorphinan-6-one Hydrochloride (Compound 7D)

A mixture of Compound 7C (6.00 g, 18 mmole; prepared in Example 7C), sodium bicarbonate (3.60 g, 43 mmole) and cyclobutylmethyl bromide (3.20 g, 21 mmole; prepared according to Neth. Appl. 6,613,986; Chem. Abst. 68: 59608m, [1968]) in 60 ml of DMF was heated in an oil bath at 100° for about 16 hrs under an argon atmosphere. The suspension was cooled and filtered and the filtrate was evaporated to give a semisolid residue. The residue was suspended in chloroform and then extracted with a dilute ammonium hydroxide solution. The aqueous phase was then extracted with two portions of chloroform, and the combined organic phases were dried, filtered and evaporated to give 6.17 g of a brown syrup. The syrup was dissolved in ethanol and an excess of concentrated HCl added. Evaporation of this solution followed by repeated addition and evaporation of ethanol gave crystals which were collected. Air drying gave 4.96 g of Compound 7D.HCl as white needles, mp sinters 200°, melts 202°–205°.

Anal. Calcd. for C$_{23}$H$_{29}$NO$_3$.HCl: C, 68.39; H, 7.48; N, 3.47; Cl, 8.78. Found: C, 68.70; H, 7.40; N, 3.53; Cl, 8.57.

E.
17-Cyclobutylmethyl-4,5α-epoxy-3-hydroxy-8β-methylmorphinan-6-one Hydrochloride (TR-5088)

A solution of Compound 7D.HCl (600 mg; prepared in Example 7D) in 2.5 ml of 48% HBr was heated at reflux for 7 min. The acidic solution was made basic by the addition of concentrated NH$_4$OH and extracted with three portions of chloroform. Evaporation of the chloroform gave 280 mg of a syrup which was chromatographed over Silica Gel G (50 g) using 10:1 V/V chloroform-methanol. Pure fractions were combined to give 230 mg of a foam which was converted to the HCl salt as in Example 1A. Crystallization from ethanol-ethyl acetate gave pure TR-5088.HCl, mp 220°–225°.

Anal. Calcd for C$_{22}$H$_{27}$NO$_3$ HCl: C, 67.77; H, 7.24; N, 3.59; Cl, 9.09. Found: C, 67.47; H, 7.32; N, 3.56; Cl, 9.39.

EXAMPLE 8

This example describes the preparation of 17-cyclobutylmethyl-4,5α-epoxy-3-hydroxymorphinan-6-one (reference Compound TR-5128) and its intermediates.

A. 4,5α-Epoxy-3-methoxy-17-methylmorphinan-6-one (Compound 8A)

A solution of 1 g of codeinone (prepared by the method of Gavard et al., Bull. Soc. Chim. Fr., 486 (1965)) in 25 ml of 95% ethanol was adjusted to about pH 1 with concentrated hydrochloric acid and was hydrogenated on a Paar apparatus at 50 psi using 200 mg of 10% Palladium on charcoal catalyst for about 1 hour. The catalyst was then removed by filtration and the filtrate was evaporated to give a solid residue. This residue was dissolved in water and the solution adjusted to about pH 11 with concentrated ammonium hydroxide solution. The basic solution was extracted with three portions of chloroform. The combined organic extracts were washed with water, dried over MgSO$_4$ and evaporated to leave a solid residue. The residue was crystallized from absolute ethanol to give the product, which had a melting point of 191°–194° C., in 87% yield.

B. 17-Cyano-4,5α-epoxy-3-methoxymorphinan-6-one (Compound 8B)

Compound 8B was prepared as described in Example 1B substituting Compound 8A for Compound 1A. The crystalline Compound 8B, mp 213°–221° C., was obtained in 87% yield. Ir:N—CN 2200 cm$^{-1}$.

C. 4,5α-Epoxy-3-methoxymorphinan-6-one (Compound 8C)

A suspension of 1 g of Compound 8B (prepared in Example 8B) in 30 ml of 2 N HCl was refluxed for about 5 hours. The solution was azeotropically distilled with ethanol to give crystalline 8C as the HCl salt, mp about 265° C., in 83% yield.

D. 17-Cyclobutylmethyl-4,5α-epoxy-3-methoxymorphinan-6-one Hydrobromide(TR-5108)

A mixture of 5.50 g of Compound 8C (17.1 mmole; prepared in Example 8C), 3.2 g of NaHCO₃ (37.6 mmole), and 3.82 g of cyclobutylmethyl bromide (25.6 mmole); prepared according to Neth. Appl. 6,613,986; Chem. Abst. 68: 59608 m [1968]) in 50 ml of DMF was heated under argon at 100° C. for 16 hours. Treatment of the reaction mixture as in Example 1D gave a syrup. The syrup was converted to the HBr salt according to the method of Example 1A, substituting HBr for HCl, and the salt (3.20 g, 43% yield) was crystallized from ethanol-ethyl acetate. Recrystallization from the same solvent gave Compound 8D.HBr mp 232°–233° C.

Anal. Calcd. for $C_{22}H_{27}NO_3 \cdot HBr$: C, 60.83; H, 6.36; N, 3.23. Found: C, 60.48; H, 6.34; N, 3.10.

E. 17-Cyclobutylmethyl-4,5α-epoxy-3-hydroxymorphinan-6-one (TR-5128)

A 3.0 g sample of Compound 8D (prepared in Example 8D) and 9 g of pyridine hydrochloride was heated at about 170° C. for 1 hour. The mixture was cooled, water was added and the solution was extracted with several portions of methylene chloride. The organic extracts were combined, dried, filtered and evaporated to give 1.86 g of a dark foam. The foam was twice chromatographed over Silica Gel G using 8:1 V/V chloroform-methanol as the eluent. The desired product was obtained as a white foam.

Anal. Calcd. for $C_{21}H_{25}NO_3$: C, 74.31; H, 7.43; N, 4.13. Found: C, 70.14; H, 6.95; N, 3.82.

The preparation of the compounds corresponding to Formula I'0 where R₃ is α-ethyl is illustrated by the following Scheme I and Example 9 in which the numerical designations of compounds correspond one with the other.

Investigation of the residual mother liquors form the lithium dialkyl cuprate reactions revealed, in addition to the major 8β alkylated product, the presence of a minor 8α-alkylated derivative and a 4,5-epoxy cleaved product. This minor α isomer could be isolated by careful column chromatography in low yield. The minor isomers usually account for about 2 to 8% of the total reaction product.

The structure of the minor α isomers was proven by mass spectral and nuclear magnetic resonance techniques. Most important, for the 8α-ethyl isomer (3, scheme I) is that the nuclear magnetic resonance signal in the terminal methyl in the 8α-ethyl group is shifted upfield relative to that of this signal for the 8β-ethyl group in 2. This shielding effect can occur only when the 8-alkyl group is in the α or axial orientation and is caused by the anisotropic effect of the aromatic A ring.

After isolation of sufficient 8α-ethyl product 3, this monomer was converted to potential mixed analgesics/-narcotic antagonists in a manner similar to that described supra for the 8β isomers. Thus, the N-methyl group of 3 was removed by the cyanogen bromide-acid hydrolysis sequence to give nor compound 6. The free base of 6 was alkylated with the appropriate cycloalkylmethyl bromide to give 7 and 8. The 3-methoxy group was cleaved to yield the 3-hydroxy compounds 9 and 10 by treatment with boron tribromide in chloroform solution in a manner similar to that reported by K. C. Rice, J. Med. Chem., 20, 164, 1977.

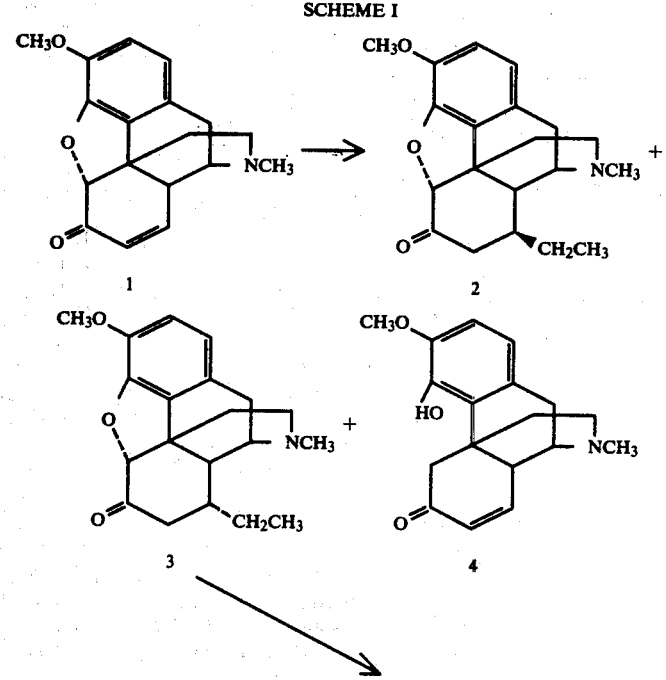

SCHEME I

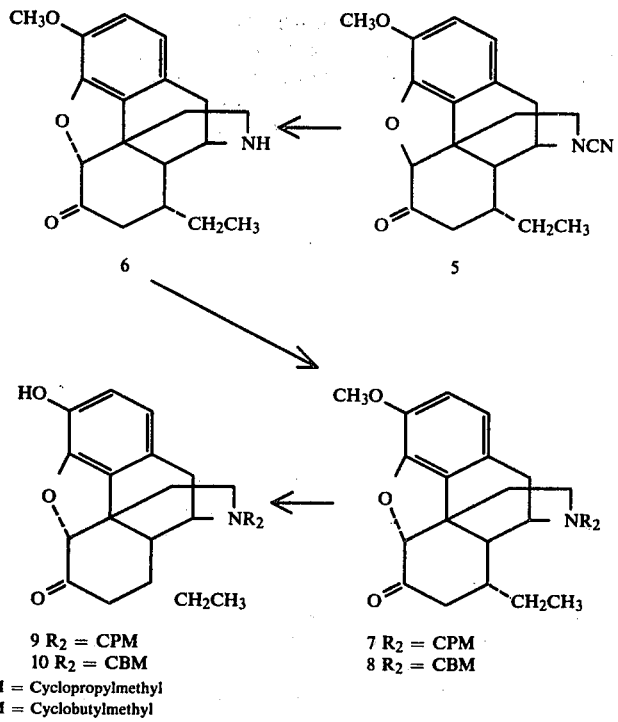

9 R₂ = CPM
10 R₂ = CBM

7 R₂ = CPM
8 R₂ = CBM

CPM = Cyclopropylmethyl
CBM = Cyclobutylmethyl

EXAMPLE 9

This example describes preparation of intermediates as well as compounds 7–10 of Scheme I.

A.
4,5α-Epoxy-8α-ethyl-3-methoxy-17-methylmorphinan-6-one (3)

The mother liquor remaining after removal of the crystals of the 8β isomer 2, Example 1Al, was evaporated to a dry residue which was chromatographed over Silica Gel G (600 g) using 6:1 chloroform-alcohol. After elution of additional 2, fractions containing 3 were eluted followed by a mixture of 3 and thebainone-A (4). Fractions containing only 3 were combined and crystallized from ethyl acetate to give white crystals of 3, mp 188.5°–190°. NMR: δ 6.68, narrow d, 2H, (aromatic, J=1 Hz; 4.72, s, 1H (H-5); 3.90, s (CH₃O—); 2.45, s (CH₃N—), 0.86–0.46, t, 3H (methyl group on 8α-ethyl side chain).

Anal. Calcd for $C_{20}H_{25}NO_3$; C, 73.37; H, 7.70; N, 4.28. Found: C, 73.36; H, 7.76; N, 4.12.

B.
17-Cyano-4,5α-epoxy-8α-ethyl-3-methoxymorphinan-6-one (5)

4,5α-Epoxy-8α-ethyl-3-methoxy-17-methylmorphinan-6-one 3 (6.50 g, 19.8 mmole) was dissolved in chloroform (100 ml). After the addition of $K_2CO_3$ (4.12 g, 29.8 mmole), the stirred suspension was treated dropwise with a solution of cyanogen bromide (2.50 g, 23.8 mmole) in 50 ml of chloroform. After the addition was complete, the mixture was heated to reflux and refluxed for 2 hours. Cooling was followed by removal of the insoluble material by filtration. The filtrate was evaporated to a residue which crystallized on coevaporation with ethanol. The crystals were suspended in hot ethanol, the mixture cooled and the crystals collected to give 6.30 g (94%) of 5 as white needles, mp 212°–217°, in two crops.

C. 4,5α-Epoxy-8α-ethyl-3-methoxyorphinan-6-one (6)

A suspension of 17-cyano-4,5α-epoxy-8α-ethyl-3-methoxymorphinan-6-one 5 (6.30 g) in 150 ml of 2 N HCl was refluxed for five hours. The resulting clear solution was cooled, adjusted to pH ~11 by the addition of concentrated $NH_4OH$ and extracted with three portions of chloroform. The chloroform extracts were dried and evaporated to give 5.8 g of 6 as a glass which was used in alkylation experiments without further purification.

D.
17-Cyclopropylmethyl-4,5α-epoxy-8α-ethyl-3-methoxymorphinan-6-one Tartrate (7, TR-5427)

A mixture of 4,5α-epoxy-8α-ethyl-3-methoxymorphinan-6-one (2.80 g, 8.9 mmole), $NaHCO_3$ (1.88 g, 22.3 mmole) and cyclopropylmethyl bromide (1.45 g, 10.7 mmole) in 60 ml of DMF was heated in an oil bath at 100° for 2 hours under an argon atmosphere. The cooled suspension was filtered and the filtrate evaporated to a semi-solid residue. The residue was partitioned between dilute ammonia and toluene. Evaporation of the toluene gave a syrup which was chromatographed to give 2.21 g (67%) of the free base of 7 as a foam. This foam was converted to the d-tartrate salt by dissolving the free base in ethanol and adding a solution of d-tartaric acid (1 equivalent) in ethanol. The product crystallized on cooling of the solution. Pure 7, mp sinters 140°, melts 150°–160°, isolated by filtration, analyzed as the hemi-hydrate.

Anal. Calcd for $C_{23}H_{29}NO_3 \cdot C_4H_6O_6 \cdot 0.5H_2O$; C, 61.59 H, 6.89; N, 2.66. Found: C, 61.69; H, 6.75; N, 2.78.

E.
17-Cyclobutylmethyl-4,5α-epoxy-8α-ethyl-3-methoxymorphinan-6-one Tartrate (8, TR-5428)

A mixture of 6 (3.05 g, 9.7 mmole), NaHCO$_3$ (2.05 g, 24.3 mmole) and cyclobutylmethyl bromide (1.74 g, 11.7 mmole) in DMF (65 ml) was heated at 100° for 16 hours. The reaction was processed as described before and 2.23 g (60%) of the free base of 8 isolated after chromatography. This was converted to the d-tartrate salt and recrystallized from ethanol to yield 8 as the hemi-hydrate.

Anal. Calcd for C$_{24}$H$_{31}$NO$_3$.C$_4$H$_6$O$_6$.0.5H$_2$O: C, 62.21, H, 7.09; N, 2.59. Found: C, 62.03; H, 6.87; N, 2.40.

F.
17-Cyclopropylmethyl-4,5α-epoxy-8α-ethyl-3-hydroxymorphinan-6-one Hydrochloride (9, TR-5436)

A solution of the free base of 7, 17-cyclopropylmethyl-4,5α-epoxy-8α-ethyl-3-methoxymorphinan-6-one, (1.78 g, 4.8 mmole) in chloroform was added to a solution of boron tribromide (2.76 ml, 29 mmole) in chloroform (75 ml) with maintenance of the temperature at about 20° while under an argon atmosphere. The mixture was stirred for 20 minutes at room temperature, then cooled in an ice bath. Methanol (10 ml) was then added rapidly dropwise. After completion of this addition the solution was evaporated to dryness. The residue was partitioned between dilute NH$_4$OH and chloroform. The organic phase was separated and the aqueous phase washed with three portions of chloroform. The combined organic phases were evaporated and the residue purified by chromatography to give 1.27 g (74%) of the free base of 9. This was converted to the HCl salt in the usual fashion which was twice crystallized from methanol-ethyl acetate to give pure 9, mp 235°-250° dec., which analyzed as the hemi-hydrate.

Anal. Calcd. for C$_{22}$H$_{27}$NO$_3$.HCl.0.5H$_2$O: C, 66.24; H, 7.33; N, 3.51. Found: C, 66.49; H, 7.35; N, 3.69.

G.
17-Cyclobutylmethyl-4,5α-epoxy-8α-ethyl-3-hydroxymorphinan-6-one Hydrochloride (10, TR-5437)

This compound was pepared by treatment of the free base of 8 (1.71 g, 4.5 mmole) with boron tribromide (2.6 ml, 27 mmoles) in chloroform as reported above. Workup followed by chromatography gave 757 mg (46%) of the free base of 10 as a foam. This was converted to the HCl salt which crystallized to give pure 10, mp>265°, as the hemi-hydrate.

Anal. Calcd. for C$_{23}$H$_{29}$NO$_3$.HCl.0.5H$_2$O: C, 66.90; H, 7.57; N, 3.39. Found: C, 66.52; H, 7.39; N, 3.64.

The 7-substituted compounds which are claimed in this patent application differ from the known analgesic agents dihydromorphinan and dihydrocodeinone and the mixed narcotic agonist-antagonists, N-cyclopropylmethyl-dihydrocodeinone and -dihydromorphinone, by the presence of a methyl group in the 7α-position and optionally, a methyl group in the 8β-position. One compound of this series, 7α-methyl-N-cyclopropylmethyl dihydromorphinone (17-cyclopropylmethyl-4,5α-epoxy-3-hydroxy-7α-methylmrophinan-6-one, TR-5402) has an especially useful agonist-antagonist potency (ED$_{50}$=0.42, AD$_{50}$=1.63).

The preparation of those compounds which are generally characterized by Formula I when R$_4$ is α-methyl and R$_2$ is cyclopropylmethyl or cyclobutylmethyl is described by Scheme II and Example 10 which follow. Referring to Scheme II, thebaine 12 is reacted with lithium dimethyl cuprate to yield 3,6-dimethoxy-7β,17-dimethyl-4-hydroxy-5,6,8,14-tetradehydro-morphinane 13 which is hydrolyzed to a mixture of B/C cis and trans α,β-unsaturated ketones 14 and 15. The minor product of this reaction, the B/C trans compound 15 will not undergo ring closure and is most conveniently separated from the desired cis isomer 14 at this stage by chromatography. Compound 14 is then reduced to the 7α-methyl derivative 16a by catalytic means or reacted with lithium dimethyl cuprate to give 16b. The introduction of the 8-methyl group requires an excess of the organo copper reagent (2.5 equivalents) over that normally needed (1.25 equivalents) to effect conjugate addition to codeinone.

The 17-methyl group is displaced with a cyano function using conditions similar to those described previously, except, that in order to obtain a clean conversion to the cyano compound 17, an excess of cyanogen bromide must be utilized (2.4 verses 1.25 equivalents). Hydrolysis to the nor compounds 18 proceeds normally in refluxing 2 N HCl. The nor compounds 18 are alkylated using cyclopropylmethyl or cyclobutylmethyl bromide under standard reaction conditions to give 19. The treatment of compounds 19 with two equivalents of bromine in glacial acetic acid yields the intermediate 1-bromo-5β-bromo compound 20 which is not isolated. This intermediate, in chloroform solution, is treated with cold dilute aqueous sodium hydroxide. The anion of the 4 hydroxy group displaces the 5β-bromine in an SN$_2$ fashion resulting in closure of the 4,5-epoxy bond to give 21. The desired compounds 21 are isolated by chromatography in about 50% yield. Other higher brominated analogs are the major contaminating products.

Compounds 21 are debrominated by hydrogenation in aqueous buffer utilizing conditions similar to those described by Rapoport, J. Med. Chem., (9, 1171, 1976), ie, aqueous sodium acetate buffer at pH~4.5. Hydrogenation in neutral or acidic solution leads to substantial quantities of ring cleaved product 19. The 3-methoxy group of 22 can be cleaved to give the 3-phenol 23 in low to moderate yields by use of boron tribromide. The major contaminant in this reaction is a 4,5-epoxy cleaved product which again reflects the lability of the epoxy bond.

SCHEME II
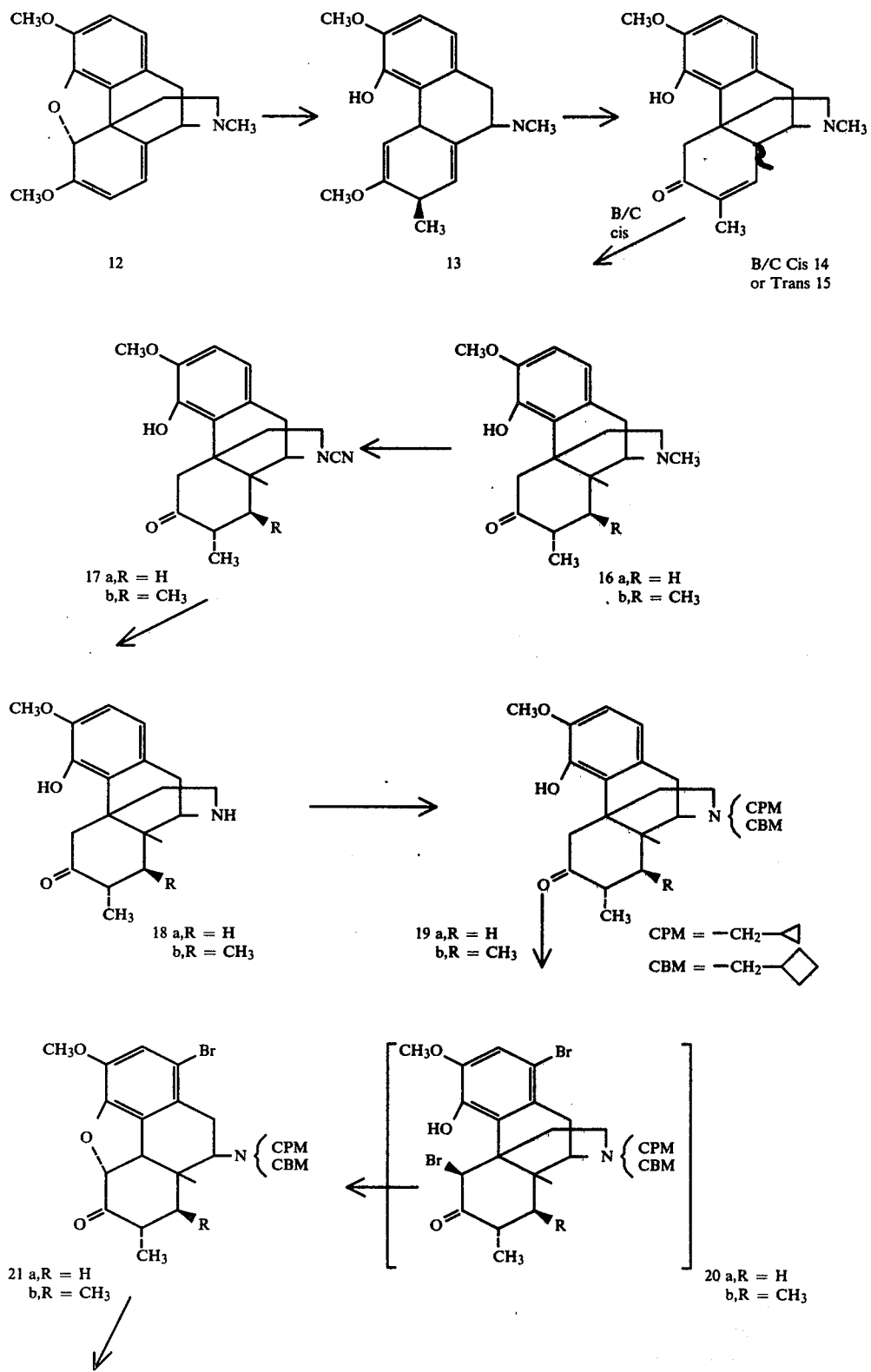

-continued
SCHEME II

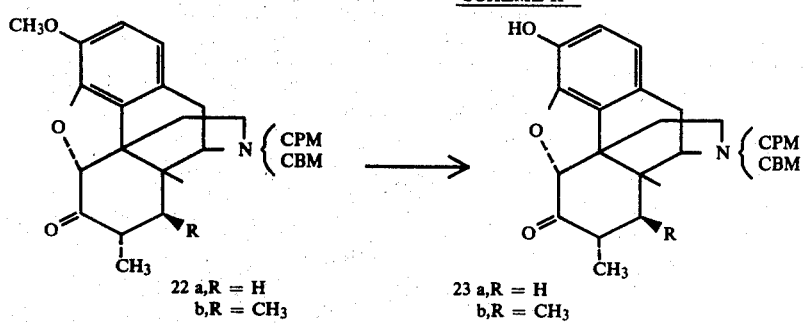

22 a, R = H
  b, R = CH₃

23 a, R = H
  b, R = CH₃

In the following examples, which describe the preparation of those compounds of the present invention which contain a 7α-methyl group, the numbering of particular compounds is designed to correspond with that used in Scheme II.

EXAMPLE 10

A.
7,8-Didehydro-7,17-dimethyl-4-hydroxy-3-methoxymorphinan-6-one (14)

Lithium dimethyl cuprate was prepared in ether (1 liter) under an argon atmosphere below 0° from copper iodide (95.2 g, 0.5 mole) and methyl lithium (1 mole in ether). To this was added, in a thin stream, a solution of thebaine (12, 124.6 g, 0.4 mole) in methylene chloride (900 ml). The mixture was stirred below 0° for 15 minutes and then allowed to warm to room temperature. Saturated NH₄Cl solution (1 liter) was added followed by concentrated NH₄OH (150 ml). After stirring for 30 minutes, the organic phase was separated and washed twice with dilute NH₄OH solution. The aqueous phase was extracted twice with methylene chloride and the combined organic phase dried and evaporated to give a foam which contained predominantly compound 13 (3,6-dimethoxy-7β,17-dimethyl-4-hydroxy-5,6,8,14-tetradehydro-morphinane).

The foam containing 13 was heated at 95° with 90% aqueous acetic acid (500 ml) for 30 minutes. The mixture was cooled in ice and then poured into concentrated NH₄OH (1 liter). This basic solution was extracted with three portions of chloroform, the organic extracts backwashed twice with dilute NH₄OH, and the organic phase dried and evaporated to a thick syrup. The syrup was fractionated by filtration through a settled slurry of Silica Gel G (400 g), packed in a large sintered glass Buchner funnel using 30:1 methanol-chloroform as the suspending media and eluting solvent. Early fractions contained a mixture of 14 to 15. Later fractions consisting mainly of 14 were pooled and evaporated to give 95 g of a foam. The foam was crystallized from ethyl acetate to give 31 g (25%) of compound 14. Recrystallization from ethyl acetate gave white needles of the hemi-ethyl acetate solvate of 14, mp 183°-185°. NMR (CDCl₃): δ 6.58, 2H (aromatic); 6.40, broad singlet, 2H(H-8 and —OH); 4.30, doublet, 1H(H-5α, J=15 Hz); 3.76, s, 3H (CH₃O—); 2.40, s, 3H(CH₃N—); 1.60, multiplet, 3H(7 CH₃—).

B. 4-Hydroxy-3-methoxy-7α-methylmorphinan-6-one (16a)

To a solution of 14 (22.0 g, 70 mmole) in 95% ethanol (200 ml) was added concentrated HCl (12 ml) and 10% palladium on activated carbon (2.0 g). The mixture was hydrogenated at an initial pressure of 50 psi until the uptake of hydrogen ceased. The mixture was filtered from the catalyst and the filtrate evaporated to a small volume. The residue was dissolved in water, the solution made basic with concentrated NH₄OH and extracted with three portions of chloroform. The chloroform extracts were washed with dilute NH₄OH, dried and evaporated to a thick syrup which crystallized on the addition of ethyl acetate. The crystals were collected and dried to give 14.4 g (65%) of 16a as white needles, mp 163°-165°. Recrystallization from acetone gave analytically pure 16a as the hemi-acetone solvate, 166°-167° NMR: δ 6.55, s, 2H (aromatic); 6.40, broad, 1H (hydroxyl H); 4.22, d, 1H (H-5α, J=13 Hz); 3.77 (CH₃O—); 2.38 (CH₃N); 0.87, d, 3H (7α-CH₃, J=6.5 Hz).

Anal. Calcd. for C₁₉H₂₅NO₃.0.5C₃H₆O: C, 71.48; H, 8.19; N, 4.07. Found: C, 71.69; H, 8.27; N, 4.12.

C.
4-Hydroxy-3-methoxy-7α,8β,17-trimethylmorphinan-6-one (16b)

Compound 14 (20.0 g, 64 mmole) in methylene chloride (400 ml) was added to a solution of lithium dimethyl cuprate (165 mmole) prepared in ether (800 ml) with cooling in an ice-salt bath under an argon atmosphere. The mixture was stirred at this temperature for 1 hour after which it was poured into saturated NH₄Cl solution (1 liter). After the addition of concentrated NH₄OH to pH ~12 and stirring for 30 minutes, the organic phase was separated and washed twice with dilute NH₄OH. The aqueous phase was extracted with additional methylene chloride and the combined organic phases dried and evaporated to give a quantitative yield of 16b as a thick syrup, NMR: δ 6.63, s, 2H (aromatic); 4.25, d, 1H (H-5α, J=13H); 3.80 (CH₃O—); 2.43 (CH₃N—); 1.08; unsymmetrical t, 3H (8β-CH₃, J=6H); 0.90, symmetrical d, 3H (7α-CH₃, J=6H). A portion of this material was converted to the hydrochloride salt by dissolving the syrupy free base in ethanol and adding excess concentrated HCl. The solution was evaporated to dryness and the residue azeotroped with ethanol, 1:1 V/V ethanol:benzene, then benzene. The residue was crystallized from ethyl acetate to give 16b HCl, mp 259°-262°.

Anal. Calcd for C₂₀H₂₇NO₃.HCl: C, 65.65; H, 7.71; N, 3.83; Cl, 9.69. Found: C, 64.01; H, 7.35; N, 3.83; Cl, 10.01.

D. 4-Hydroxy-3-methoxy-7α-methylmorphinan-6-one (18a)

To a rapidly stirred solution of 16a (13.0 g, 41.2 mmole) in chloroform (150 ml) containing powdered anhydrous potassium carbonate (8.5 g, 61.8 mmole) was added dropwise a solution of cyanogen bromide (5.5 g, 51.9 mmole) in chloroform. The mixture was stirred for 30 minutes at room temperature and then refluxed for 2 hours. The cooled mixture was filtered from solid material and the filtrate evaporated to dryness and azeotroped several times with ethanol to give a foam containing 17a. The foam was refluxed with 2 N HCl (250 ml) for 8 hours. The cooled solution was made basic with concentrated NH$_4$OH and extracted with three portions of chloroform. The chloroform extracts were processed to give 13.6 g of a foam which was chromatographed over Silica Gel G (500 g) using 3:1 chloroform-methanol containing 2% concentrated NH$_4$OH. Elution of unchanged 16a was followed by the elution of 7.3 g (59%) of 18a which was obtained as a foam. This material was used in alkylation experiments without further characterization.

E. 17-Cyano-7α,8β-dimethyl-4-hydroxy-3-methoxymorphinan-6-one (17b)

To a rapidly stirred solution of 16b (24.1 g, 73 mmole) in chloroform (250 ml) containing powdered anhydrous potassium carbonate (29.0 g, 210 mmole) was added dropwise a solution of cyanogen bromide (18.6 g, 175 mmole) in chloroform. The mixture was stirred for 30 minutes and then refluxed for 2 hours. The cooled solution was filtered to remove the insoluble material and the filtrate evaporated to dryness. After several evaporations of the residue with ethanol, crystals formed. The crystals were dissolved in boiling ethanol. After keeping overnight in the cold, 11.9 g (44%) of 17b, mp 206°–209°, was obtained from the solution in two crops.

F. 7α,8β-Dimethyl-4-hydroxy-3-methoxymorphinan-6-one (18b)

A mixture of 17b (7.50 g, 22 mmole) and 2 N HCl (225 ml) was refluxed for 7 hours. The cooled solution was made basic by the addition of concentrated NH$_4$OH and extracted with three portitons of chloroform. The chloroform extracts were dried, filtered and evaporated to give a quantitive yield of 18b as a foam, homogeneous by thin layer chromatography. This material was used without further characterization in alkylation reactions as reported below.

G. 17-Cyclopropylmethyl-4-hydroxy-3-methoxy-7α-methylmorphinan-6-one (19a-CPM)

A mixture of 18a (5.00 g, 16.6 mmole), NaHCO$_3$ (2.90 g, 34.6 mmole) and cyclopropylmethyl bromide (2.80 g, 20.8 mmole) in DMF (50 ml) was heated at 100° under argon for 2 hours. The mixture was cooled, filtered from insoluble material and the filtrate evaporated in high vacuum. The residue was dissolved in dilute NH$_4$OH and extracted with three portions of toluene. The toluene was evaporated to give 4.89 g (83%) of crystalline 19a-CPM. Two recrystallizations from ethanol gave analytically pure 19a-CPM, mp 176.5°–178°. NMR: δ 6.56, s, 2H (aromatic); 6.17, S, 1H, (hydroxy proton); 4.23, d, 1H, (H-5α, J=12.5 Hz); 3.78 (CH$_3$O—); 1.30, d, (H-5β); 0.87, d, 3H (7α-CH$_3$, J=6.5 Hz), Anal. Calcd. for C$_{22}$H$_{29}$NO$_3$: C, 74.33; H, 8.22; N, 3.94. Found: C, 74.06; H, 8.34; N, 4.01.

H. 17-Cyclopropylmethyl-7α,8β-dimethyl-4-hydroxy-3-methoxymorphinan-6-one Hydrochloride (19b-CPM)

A mixture of 18b (7.20 g, 22.8 mmole), NaHCO$_3$ (3.84 g, 45.7 mmole) and cyclopropylmethyl bromide (3.70 g, 27.4 mmole) in DMF (100 ml) was heated at 100° under argon for 2.5 hours. The mixture was processed as described for 19a-CPM to give 8.31 g (99%) of 19b-CPM as a foam. NMR: δ 6.90 (aromatic); 6.35, broad s, 1H (hydroxyl proton); 4.23 (H-5α); 3.78 (CH$_3$O—); 1.10, unsymmetrical d, (8β-CH$_3$, J=5 Hz); 0.92 symmetrical d, (7α-CH$_3$, J=6 Hz). The foam was converted to the HCl salt by dissolving the free base in ethanol, adding an excess of concentrated HCl followed by evaporation to dryness. The residue was azeotroped with 1:1 ethanol-toluene, then toluene and finally crystallized from acetone to give 8.24 g (90%) of 19b-CPM.HCl, mp 194°–195°. Recrystallization from acetone gave an analytical sample of 19b-CPM.HCl as the hemi-acetone solvate. The presence of acetone was confirmed by the nmr of 19b-CMP.HCl taken in DMSO-d$_6$.

Anal. Calcd. for C$_{23}$H$_{31}$NO$_3$.HCl.0.5C$_3$H$_6$O: C, 67.68; H, 8.10; N, 3.24. Found: C, 67.90; H, 8.09; N, 3.28.

I. 1-Bromo-17-cyclopropylmethyl-4,5α-epoxy-3-methoxy-7α-methylmorphinan-6-one (21a-CPM)

To a stirred solution of 19a-CPM (3.59 g, 10 mmole) in glacial acetic acid (70 ml) was added slowly dropwise a solution of bromine (1.0 ml, 20 mmole) in acetic acid (20 ml) over a 45 minute period. The mixture was stirred for 1.5 hour and then concentrated to a thick syrup in vacuo at 45°–50°. The syrup was dissolved in chloroform (100 ml) and added to a solution of 1 N NaOH (100 ml) stirred in an ice bath. The mixture was adjusted to pH 14 by the use of additional 50% NaOH and then stirred for 10 minutes in the cold. The chloroform layer was separated, the aqueous phase washed twice more with chloroform and the combined organic phases backwashed with dilute NH$_4$OH. The dried organic phase was evaporated to give 4.98 g of a white foam which was chromatographed on Silica Gel G (400 g) using 15:1 chloroform-methanol containing 0.5% concentrated NH$_4$OH as the eluant. Homogeneous fractions containing the major product were pooled to give 2.43 g (56%) of 21a-CPM as a foam. NMR: δ 6.92; 1H, s (H-2); 4.68, 1H, s (H-5); 3.93 (CH$_3$O—); 3.16, 1H, broad; 0.96, 3H, d (7α-CH$_3$, J=6.5 Hz).

J. 1-Bromo-17-cyclopropylmethyl-7α,8β-dimethyl-4,5α-epoxy-3-methoxymorphinan-6-one (21b-CPM)

The HCl salt of 19b-CPM (5.20 g, 12.8 mmole) was converted to the free base and dissolved in glacial acetic acid (100 ml). To this solution was added dropwise over a 45 minute period, a solution of bromine (1.3 ml, 28 mmole) in acetic acid (25 ml). Stirring was continued for 1 hour after which the mixture was evaporated to a foam at 45°–50°. The foam was dissolved in chloroform (150 ml) and added to rapidly stirred 1 N NaOH (100 ml) cooled in an ice bath. After 10 minutes, the chloroform layer was separated, the aqueous phase washed with two additional portions of chloroform and the combined organic phases backwashed, dried and evaporated to give 6.23 g of a foam. The foam was chromatographed (500 g of gel, 20:1 chloroform-methanol containing 0.5% concentrated NH4OH). Fractions containing the major product which were homogeneous by thin layer chromatography were combined to give 3.32 g (58%) of 21b-CPM as a foam. NMR: δ 6.87, 1H, s (aromatic); 4.72, 1H, s (H-5); 3.93 (CH3O—); 3.73, 1H, broad; 1.04–0.90, 6H, sharp multiplet (7α,8β CH3's).

K.
17-Cyclobutylmethyl-4,5α-epoxy-3-methoxy-7α-methylmorphinan-6-one Hydrochloride (22a-CPM) (TR-5394)

Compound 20a-CPM (1.90 g, 4.4 mmole) was hydrogenated in the presence of 10% palladium on activated carbon (400 mg) in a mixture of ethanol (50 ml) and 2 N acetic acid −1.5 N sodium acetate (150 ml) at 50 psi for 2 hours. After removal of the catalyst by filtration, the filtrate was cooled and made basic by the addition of concentrated NH4OH. The solution was extracted with three portions of chloroform, the combined organic phases backwashed, dried and evaporated to give 1.55 g (100%) of the free base of 22a-CPM as a foam, homogeneous by thin layer chromatography. NMR: δ 6.60, 2H, sharp narrow doublet (aromatic, J=1 Hz); 4.65, 1H, s (H-5); 3.92 (CH3O—), 3.42, 1H, broad; 0.96, 3H, symmetrical doublet (7α-CH3, J=6 Hz). This material was converted to the HCl salt which was crystallized from acetone containing several drops of water to give 22a-CPM HCl as the hemi-hydrate.

Anal. Calcd. for $C_{22}H_{27}NO_3 \cdot HCl \cdot 0.5H_2O$; C, 66.27; H, 7.33; N, 3.50. Found: C, 66.31; H, 7.56; N, 3.52.

L.
17-Cyclopropylmethyl-7α,8β-dimethyl-4,5-epoxy-3-methoxymorphinan-6-one Hydrochloride (22b-CPM) (TR-5410)

A solution of 14 (3.32 g, 7.42 mmole) in ethanol (50 ml) and 2 N acetic acid-1.5 N sodium acetate buffer (150 ml) was hydrogenated in the presence of 10% palladium on activated carbon (0.70 g) at 50 psi for 2 hours. The catalyst was removed by filtration, the filtrate cooled and made basic by the addition of excess concentrated NH4OH. The mixture was extracted with three portions of chloroform, the combined extracts backwashed with dilute NH4OH, dried and evaporated to give 2.55 g (93%) of the free base of 22b-CPM as a glass, homogeneous by thin layer chromatography. NMR: δ 6.62, 2H, sharp doublet (aromatic, J<1 Hz); 4.67, 1H, s (H-5); 3.92 (CH3O—); 3.63, 1H, broad; multiplet for 6H centered at 0.97 for 7α,8βmethyl group. This glass was converted to the HCl salt which crystallized from ethanol to give pure 22b-CPM.HCl, mp 256°–258°.

Anal. Calcd. for $C_{23}H_{29}NO_3 \cdot HCl$: C, 68.39; H, 7.49; N, 3.47. Found: C, 68.06, H, 7.34; N, 3.43.

M.
17-Cyclopropylmethyl-4,5α-epoxy-3-hydroxy-7α-methylmorphinan-6-one (23a-CPM) (TR-5402)

To a solution of BBr3 (1.6 ml, 4.26 g, 17 mmole) in chloroform (40 ml) cooled to 20° under argon was added rapidly a solution of 22a-CPM.HCl.0.5 H2O (1.00 g, 2.5 mmole) in chloroform (30 ml) with control of the temperature at 20°. The cooling bath was removed and the suspension stirred for 15 minutes at ambient temperature. The suspension was then poured into an ice-concentrated NH4OH (20 ml) slurry and stirred for 20 minutes. The resulting suspension was extracted with four portions of chloroform and the cloudy chloroform extracts washed with dilute ammonia, dried and evaporated to give 680 mg of a foam. The foam was chromatographed (60 g of gel, 10:1 chloroform-methanol containing 1% concentrated NH4OH). After elution of unreacted starting material 250 mg (30%) of 23a-CPM was obtained a foam. NMR: δ 6.67, 2H, d (aromatic J=3 Hz); 4.70, s (H-5); 0.93, 3H, d (7α-CH3, J=7 Hz). This foam was crystalized from isopropyl alcohol to give TR-5402, mp 209–211.

Anal. Calcd. for $C_{21}H_{25}NO_3$ C, 74.31; H, 7.42; N, 4.13. Found: C, 73.65; H, 7.99; N, 4.15.

N.
17-Cyclopropylmethyl-7α,8β-dimethyl-4,5α-epoxy-3-hydroxymorphinan-6-one Hydrochloride (23b-CPM) (TR-5416)

A solution of the free base of 22b-CPM (1.77 g, 4.38 mmole) in chloroform (25 ml) was added under argon to a stirred solution of BBr3 (30 mmoles) in chloroform (40 ml) at 20°. The mixture was stirred at room temperature for 20 minutes and then poured into a slurry of ice and concentrated ammonia. After 5 minutes the organic phase was separated and the basic aqueous phase washed several times with chloroform. The chloroform extracts were processed in the usual fashion to give 1.32 g of a foam. The foam was chromatographed to give 887 mg (66%) of the free base of 23b-CPM as a foam. NMR: δ 4.70, s, 1H, H-5. The foam was converted to the HCl salt which was dissolved in hot acetone, the solution cooled and 23b-CPM.HCl precipitated by the addition of ether.

Anal. Calcd. for $C_{22}H_{27}NO_3 \cdot HCl$: C, 67.77; H, 7.24; N, 3.59. Found: C, 66.38; H, 7.24; N, 3.62.

O.
17-Cyclobutylmethyl-4-hydroxy-3-methoxy-7α-methylmorphinan-6-one (19a-CMB)

Prepared by reaction of 18a (3.70 g, 12.3 mmole) with cyclobutylmethyl bromide (2.24 g, 14.7 mmole) in the presence of NaHCO3 (2.00 g, 25 mmole) in DMF (50 ml) at 100° under argon for 6 hours to give, after processing in the usual manner, 4.50 g (99%) of 19a-CBM as a foam. NMR: δ 6.60; 2H, s (aromatic); 5.5, 1H, broad (hydroxyl), 4.24, 1H, d (H-5α, J=13 Hz); 3.76 (CH3O—), 0.86, 3H, d(7α-CH3, J=6.5 Hz).

P.
17-Cyclobutylmethyl-7α,8β-dimethyl-4-hydroxy-3-methoxymorphinan-6-one (19b-CBM)

Prepared by reaction of 18b (11.46 g, 36.3 mmole) with cyclobutylmethyl bromide (6.50 g, 43.6 mmole) in the presence of NaHCO3 (6.10 g, 72.6 mmole) in DMF (150 ml) at 100° for 8 hours. Processing as previously described gave 11.79 g (85%) of 19b-CMB as a foam which was converted to the HCl salt, which crystallized from acetone to give 8.07 g of 19b-CBM HCl as white crystals, mp 181°–187° containing 0.5 mole of acetone as indicated by the nmr spectra of this salt in DMSO d6.

Anal. Calcd. for $C_{24}H_{33}NO_3 \cdot HCl \cdot 0.5C_3H_6O$; C, 68.23; H, 8.28; N, 3.25. Found: C, 68.07; H, 8.11; N, 3.29.

Q.

1-Bromo-17-cyclobutylmethyl-4,5α-epoxy-3-methoxy-7α-methylmorphinan-6-one (21a-CBM)

To a solution of 19a-CBM (4.39 g, 11.87 mmole) in glacial acetic acid (100 ml) was added slowly dropwise over a 45 minute period, a solution of bromine (1.2 ml, 24 mmole) in glacial acetic acid (20 ml). The mixture was stirred for 45 minutes and then evaporated at 45°–50° to a syrup. The syrup was dissolved in chloroform (100 ml) and poured into rapidly stirred cold 1 N NaOH (150 ml). After stirring for 10 minutes, the chloroform layer was separated. The aqueous phase was washed with two additional portions of chloroform, the combined organic extracts backwashed, dried and evaporated to give a foam which was chromatographed (500 g of gel, 25:1 chloroform-methanol containing 0.5% concentrated NH₄OH). Pure fractions containing the major spot were pooled and evaporated to give 2.87 g (54%) of 21a-CBM as a foam. NMR: $\delta$ 6.87 g 1H (aromatic); 4.64, 1H, s, (H-5), 3.90 (CH$_3$O—), 3.17, 1H, broad; 0.97; 3H, d (7α-CH$_3$, J=6.5 Hz).

R.

1-Bromo-17-cyclobutylmethyl-7α,8β-dimethyl-4,5α-epoxy-3-methoxymorphinan-6-one (21b-CBM)

Compound 19b-CBM HCl (6.00 g, 14.3 mmole) was converted to the free base, dissolved in glacial acetic acid and treated with a solution of bromine (1.5 ml, 30 mmole) in acetic acid (25 ml) as previously described. Further processing and reaction with sodium hydroxide as described before gave a foam which was chromatographed to give 2.20 g (33%) of 21b-CMB as a foam. NMR: $\delta$ 6.83, 1H (aromatic), 4.67, 1H (H-5) 3.90 (CH$_3$O—); 3.43, 1H, broad; 0.94, 6H, complex multiplet (7α,8β-CH$_3$).

S.

17-Cyclobutylmethyl-4,5α-epoxy-3-methoxy-7α-methylmorphinan-6-one Hydrochloride (22a-CBM) (TR-5403)

Compound 21a-CBM (2.77 g, 6.20 mmole) in ethanol (50 ml) and HOAc-NaOAc buffer (100 ml) containing 10% palladium on activated carbon was hydrogenated at 50 psi and processed as previously described to give 2.12 g (93%) of 22a-CBM as a foam. NMR: $\delta$ 6.65, 2H, sharp d (aromatic J<1 Hz); 4.63, 1H, s, (H-5); 3.93, 3H (CH$_3$O—), 0.97, 3H, d (7α-CH$_3$, J=6.5 Hz). The foam was converted to the HCl salt which crystallized from methanol-ethyl acetate. The hygroscopic material obtained was recrystallized from the same solvent pair to give hygroscopic, crystalline 22a-CMB.HCl which analyzed as the hemi-hydrate.

Anal. Calcd. for C$_{23}$H$_{29}$NO$_3$.HCl.0.5H$_2$O: C, 66.93; H, 7.57; N, 3.40. Found: C, 66.99; H, 7.47; N, 3.40.

T.

17-Cyclobutylmethyl-7α,8β-dimethyl-4,5α-epoxy-3-methoxymorphinan-6-one (22b-CBM)(TR-5429)

Compound 21b-CBM (2.10 g, 4.56 mmole) in ethanol (50 ml) and acetate buffer (150 ml) was hydrogenated in the presence of 10% palladium on carbon (0.50 g). Processing in the usual fashion gave a quantitative yield of 22b-CBM. This material could not be induced to crystallize as the free base or HCl salt. The free base was chromatographed and obtained as a foam for analysis.

Anal. Calcd. for C$_{24}$H$_{31}$NO$_3$: C, 75.56; H, 8.19; N, 3.67. Found: C, 74.71; H, 8.08; N, 3.86.

U.

17-Cyclobutylmethyl-4,5α-epoxy-3-hydroxy-7α-methylmorphinan-6-one Hydrochloride (23a-CBM)(TR-5404)

A solution of the free base of 22a-CMB (1.03 g, 2.8 mmole) in chloroform (30 ml) was added to a solution of boron tribromide (1.6 ml) in chloroform (30 ml) at 20° under argon. The mixture was stirred for 20 minutes and then poured into a slurry of ice and concentrated NH$_4$OH (20 ml). The mixture was stirred for 20 minutes, the layers separated and the aqueous phase extracted with two additional portions of chloroform. The combined organic phases were backwashed, dried and evaporated to give 1.00 g of a foam. The foam was chromatographed over Silica Gel G (75 g) using 8:1 chloroform-methanol containing 1% concentrated NH$_4$OH as the eluant to give 558 mg (56%) of 23a-CBM as a foam which could not be crystallized. The foam was converted to the HCl salt and finally dissolved in ethanol, treated with charcoal, filtered and evaporated to a foam which was dried for analysis. Compound 23a-CBM.HCl best analyzed as a hemi-hydrate.

Anal. Calcd. for C$_{22}$H$_{29}$NO$_3$.HCl.0.5H$_2$O: C, 66.27; H, 7.32; N, 3.51. Found: C, 66.33; H, 7.24; N, 3.33.

V.

17-Cyclobutylmethyl-7α,8β-dimethyl-4,5α-epoxy-3-hydroxymorphinan-6-one (23b-CBM)(TR-5430)

A solution of the free base 22b-CBM (690 mg, 1.8 mmole) in chloroform (10 ml) was added to a solution of boron tribromide (1.0 ml) in chloroform (20 ml) under argon. The resulting mixture, containing an insoluble gum, was kept at room temperature for 20 minutes, then cooled in an ice bath. Methanol (5 ml) was added slowly dropwise to give a clear solution which was concentrated to a small volume. The solution was diluted with aqueous ammonia and extracted five times with chloroform. The chloroform extracts were processed in the usual fashion to give 913 mg of a brown foam. This foam was chromatographed to give 413 mg (62%) of 23b-CBM as a foam. The foam was dried in high vacuum for analysis.

Anal. Calcd. for C$_{23}$H$_{29}$NO$_3$.H$_2$O: C, 71.66; H, 8.11; N, 3.63. Found: C, 72.62; H, 8.01; N, 3.28.

PHARMACOLOGICAL EVALUATION

The compounds whose preparation is disclosed in the foregoing examples were screened to determine the following biological activities:

(A) Analgesic effects upon mice (acetic acid writhing test).

(B) Narcotic antagonist activity in rats (modified rat tail flick test).

TEST A. ACETIC ACID MOUSE WRITHING TEST

The analgesic effects of test compounds were determined in mice by use of the acetic acid writhing test described by B. J. R. Whittle, Brit. J. Pharmacol., 22:246 (1964). In this test at least three groups of five male CD-1 mice (18–22 g) each were given subcutaneous doses of the test drug dissolved in either distilled water or distilled water acidified with HCl depending on the solubility of the compound. In all cases, 0.4 milliliter of a 0.5% V/V acetic acid in distilled water solution was administered intraperitoneally 15 minutes post drug. The number of writhes in a 20 min. interval beginning 5 minutes after the acetic acid injection were determined and compared with the number of writhes in control groups which had received only acetic acid.

Percent inhibition of writhing was calculated as:

$$\% \text{ inhibition} = \frac{\text{No. Control writhes} - \text{No. treated writhes}}{\text{No. control writhes}} \times 100$$

The ED$_{50}$ dose, i.e., the dose required to reduce the number of writhes by 50%, was determined graphically from a plot of % inhibition as a probit versus log dose. Confidence limits of 95% were calculated on the basis of those results falling in the range 16–84% inhibition. See Litchfield, J. T. and Wilcoxon, F., J. Pharmacol. Exp. Ther., 96, 99–113, (1949).

TEST B. EVALUATION OF NARCOTIC ANTAGONIST ACTIVITY

The narcotic antagonist effects of test compounds were determined by a modification of the rat tail flick procedure of Harris and Pierson (J. Pharmacol. Exp. Ther. 143,141 [1964]).

Male albino Wistar rats (100–120 g) were used for this study. A rat's tail is so placed so as to cover a photocell. Heat is applied by a lamp in a reflector with a timer being connected to the lamp and photocell so that the timer goes on when the light is turned on and is turned off when the photocell is uncovered. A rheostat, incorporated into a heating lamp is used to adjust the intensity of the light falling on the tail of the rat such that the rat's control reaction time is from two to four seconds. Animals with a control reaction time outside this range are rejected. The rheostat adjustment is made only if a significant proportion (more than 2 out of every 10 rats) of the reaction times are outside the range of two to four seconds. Groups of five rats were used each time, and two control times were determined at 60 and 30 minutes prior to subcutaneous injection of the drug. A ten second cutoff time is employed; if the rat does not flick its tail in 10 seconds it is removed from the heat source.

Thirty minutes after the last control run the test drug was given intraperitoneally. This was followed ten minutes later by an ED$_{80}$ dose of morphine subcutaneously. The animals were retested at 20 minutes after the morphine injection. Control animals were given vehicle and morphine only. The data were calculated as follows:

$$\% \text{ Effect } (E) = \frac{[\text{MRT}^* \text{ (Treated)} - \text{MRT (Control)}]}{10 - \text{MRT (Control)}} \times 100$$

$$\% \text{ Antagonism} = \frac{[E(\text{morphine controls}) - E(\text{drug treated})]}{E \text{ (morphine control)}} \times 100$$

*MRT is defined as mean reaction time.

The data were plotted on log-probit paper and AD$_{50}$ values, i.e., the dose required to inhibit the morphine effect by 50% within 95% confidence limits, were determined by the method of Litchfield and Wilcoxon.

The results of these experiments are set out in Table I where R$_1$, R$_2$, R$_3$ and R$_4$ refer to the preceding Formula I for the compounds of the present invention. In the column under R$_2$, CBM stands for cyclobutylmethyl, CPM for cyclopropylmethyl. THF stands for tetrahydrofuryl and Al for allyl. For purposes of this table, IA is intended to mean "inactive" at the dose inciated.

TABLE I

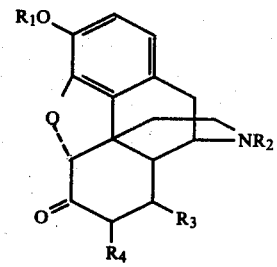

| Compound | Ex. | R$_1$ | R$_2$ | R$_3$ | R$_4$ | ED$_{50}$ (mg/kg) | AD$_{50}$ (mg/kg) |
|---|---|---|---|---|---|---|---|
| 8β- alkyl Compounds ||||||||
| TR-5109 | 1D | CH$_3$ | CPM | β-ethyl | H | 2.1 | 0.78 |
| Tr-5126 | 2 | H | CPM | β-ethyl | H | 7.8 | 0.25 |
| TR-5115 | 3B | H | CBM | β-ethyl | H | 9.2 | 0.52 |
| TR-5271 | 4B | H | THF | β-ethyl | H | 1.06 | 1.80 |
| TR-5256 | 5 | CH$_3$ | Al | β-ethyl | H | >10/0 | 5.6 |
| TR-5266 | 6 | H | Al | β-ethyl | H | IA 10 | 0.58 |
| TR-5088 | 7E | H | CBM | β-methyl | H | 0.67 | 1.9 |
| 8α-ethyl Compounds ||||||||
| TR-5427 | 9D | CH$_3$ | CPM | α-ethyl | H | >10 | >10 |
| TR-5436 | 9F | H | CPM | α-ethyl | H | 0.36 | 4.10 |
| TR-5428 | 9E | CH$_3$ | CBM | α-ethyl | H | IA 10 | IA 10 |
| TR-5437 | 9C | H | CBM | α-ethyl | H | 0.15 | >10 |
| 7α-methyl Compounds ||||||||
| TR-5394 | 10K | CH$_3$ | CPM | H | α—CH$_3$ | IA 10 | 1.60 |
| TR-5402 | 10M | H | CPM | H | α—CH$_3$ | 0.42 | 1.63 |
| TR5410 | 10L | CH$_3$ | CPM | α—CH$_3$ β—CH$_3$ | >10 | 0.98 |
| TR5416 | 10N | H | CPM | β—CH$_3$ | α—CH$_3$ | IA 10 | 0.57 |
| TR-5403 | 10S | CH$_3$ | CBM | H | α—CH$_3$ | 9.0 | 16.5* |
| TR-54:4 | 10U | H | CBM | H | α—CH$_3$ | 0.3 | 13.2 |
| TR-5429 | 10T | CH$_3$ | CBM | β—CH$_3$ | α—CH$_3$ | >10 | ~10 |
| TR-5430 | 10V | H | CBM | β—CH$_3$ | α—CH$_3$ | 5.8 | 2.5 |
| 7 and 8 Unsubstituted Reference Compounds ||||||||
| TR-5095** | | CH$_3$ | CPM | H | H | 17.0 | 3.4 |

TABLE I-continued

[Structure I: a morphinan-type skeleton with R₁O- on aromatic ring, epoxy bridge O, -NR₂ substituent, R₃ and R₄ substituents, and a ketone C=O]

| Compound | Ex. | $R_1$ | $R_2$ | $R_3$ | $R_4$ | $ED_{50}$ (mg/kg) | $AD_{50}$ (mg/kg) |
|---|---|---|---|---|---|---|---|
| TR-5118** |  | H | CPM | H | H | 1.34 | 0.19 |
| TR-5108 | 8D | $CH_3$ | CBM | H | H | 8.8 | IA.3 |
| TR-5128 | 8E | H | CBM | H | H | 0.07 | 1.7 |

*Estimated
**The preparation of these compounds is described by Gates and Montzka (J. Med. Chem., 7:127 [1964])

The above data indicates that the compounds of the present invention which are 8β-alkyl substituted are useful as narcotic antagonists and except for TR-5266 they demonstrate analgesic activity. Compound TR Nos. 5109, 5126, 5115 and 5266 are especially effective narcotic antagonists whereas compound TR Nos. 5109, 5271 and 5088 are especially effective analgesics. TR-5256 shows some mixed analgesic narcotic antagonist activity but is not particularly potent in either respect.

Of the 8α-ethyl substituted compounds, TR-5436 is of special interest due to its activity as a mixed analgesic/narcotic antagonist. This is in contrast to the other 8α-ethyl compounds which, with the exception of TR-5437 which is a pure analgesic, are not particularly active.

Of the 7α-methyl compounds, those which demonstrate especially desirable pharmacological profiles are TR-5402, TR-5430 and TR-5416 since the former two are mixed analgesics/narcotic antagonists while the latter is a pure narcotic antagonist.

C. EVALUATION BY CHARCOAL MEAL TESTS

The agonist and antagonist effects of TR-5088, reference compound TR-5128 and prior art compound 17-cyclopropylmethyl-4,5α-epoxy-3-hydroxymorphinan-6-one (TR-5118) were determined in mice by a modified procedure of Rodriguez and Villarreal (report on the 36th Annual Scientific Meeting Committee on the Problems of Drug Dependance, Mar. 10–14, 1974, Mexico City, D.F.).

Subjects and Procedure for Measuring Gastrointestinal Peristaltic Activity. The mice used were albino females of the CFW strain, weighing between 20 and 25 grams; ten animals per dose were used for each compound tested in each experiment except 20 animals were used in the tests of Compound 5088. Gastrointestinal peristaltic activity was measured using a modification of the charcoal meal method described by Macht and Baba-Gose (1931). Mice were deprived of food 18 hours before the administration of the charcoal meal. In order to facilitate clearance of gastrointestinal contents, 1 ml of physiologic saline was administered by gastric intubation 15 hours before the charcoal meal. This meal consisted of an aqueous suspension of 5% powdered tragacanth and 5% animal charcoal and was freshly made for each experiment. The charcoal meal was administered by gastric intubation, 0.25 ml per mouse. The animals were sacrificed by cervical dislocation. After the sacrifice, the whole gastrointestinal tract was rapidly removed and freed of epiploon. Then the entire length of intestine was hung upon a small hook at the level of the pylorus. In order to standardize the tension of the intestine, a 5 g weight was hung at the level of the ileocecal valve. Gastrointestinal peristaltic activity was then determined by measuring the distance the charcoal traveled from the pylorus.

Drugs. Morphine hydrochloride, naloxone hydrochloride or test compounds were each dissolved in distilled water with their concentrations adjusted so that the volume of injection was 10 ml/kg. Doses are expressed in terms of the salts.

Determination of Ability of Test Compound to Directly Inhibit Peristalsis (Agonist test).

Morphine (8 mg/kg), test compound, or saline control was administered subcutaneously (s.c.), at time 0, the charcoal meal was administered by mouth (p.o.) at time 15 min, water (10 ml/kg) was administered s.c. at time 30 min, and the animals were sacrificed at time 45 min. The saline control value represents 0% inhibition and the morphine value represents 100% inhibition. All test compounds had values between saline and morphine, and results are expressed as % inhibition compared to morphine.

The data were subjected to analysis of variance. Also the Scheffe test, a statistical test that allows for multiple comparison, was performed.

Determination of Ability of Test Compounds to Antagonize the Anti-Peristaltic Effects of Morphine (Antagonist test).

Morphine (8 mg/kg) was given s.c. at time 0, charcoal meal was given p.o. at time 15 min, naloxone or test compound was given s.c. at 30 min, and the animals were sacrificed at time 45 min. Naloxone is the standard of reference and its maximum effect (at 10 mg/kg) to antagonize the antiperistaltic effects of morphine is assigned the value of 100%; test compounds are expressed as % of maximum naloxone antagonism.

Table II provides the results obtained in the Agonist Charcoal meal test (Agonist test).

TABLE II

| Percent Inhibition of Peristalsis By Test Compound At Various Doses | | | |
|---|---|---|---|
| Dose (mg/kg) | TR-5118 | TR-5128 | TR-5088 |
| 0.01 | 24.7 | 17.5 | 13.5 |
| 0.1 | 25.4 | 35.6 | 39.8 |
| 1.0 | 40.8 | 50.7 | 50.7 |

TABLE II-continued

Percent Inhibition of Peristalsis By Test Compound At Various Doses

| Dose (mg/kg) | TR-5118 | TR-5128 | TR-5088 |
|---|---|---|---|
| 10.0 | 44.8 | 76.3 | 54.0 |
| 100.0 | 47.1 | 84.2 | 63.5 |

One of the agonist effects of morphine is the undesirable effect of producing constipation. The determination of the ability of the test compound to directly inhibit peristalsis (Agonist test) in the mouse is then a measure of the test compounds undesirable constipating side effect.

An analysis of variance for each of the compounds of Table II indicates that all compounds have an effect in inhibiting peristalsis, and that the effects of Compounds TR-5118 and TR-5088 are the same, but inhibit peristalsis to a statistically significantly less degree than TR-5128.

Table III provides the results of the test compounds ability to reverse the anti-peristaltic effects of morphine (Antagonist test).

TABLE III

Percent Reversal (S.E.*) Of Anti-Peristaltic Effects Of Morphine By Test Compound And Naloxone At Various Doses

| Dose mg/kg | Naloxone | TR-5118 | TR-5088 | TR-5128 |
|---|---|---|---|---|
| 0.01 | 14.5(±3.0) | — | — | 0.0 |
| 0.031 | — | — | 12.4(±5.8) | — |
| 0.10 | 39.1(±4.2) | — | — | 8.3(±4.6) |
| 0.31 | — | — | 27.7(±7.3) | — |
| 1.0 | 69.8(±8.0) | — | — | 13.5(±7.3) |
| 3.1 | — | 56.6(±8.0) | 54.6(±6.7) | — |
| 10.0 | 100.0(±5.9) | — | — | 19.1(±5.8) |
| 31.0 | — | 69.3(±6.4) | 44.7(±6.2) | 20.4(±5.3) |

*The values within the parentheses refer to standard error (S.E.).

The determination of the ability of the test compound to antagonize the anti-peristaltic effects of morphine (Antagonist test) in the mouse is a measure of the narcotic antagonist effect of the compound.

The data from the above two tests clearly demonstrates unexpected structure activity relationships for the compounds of this invention having a methyl group in the 8β-position. The 17-cyclopropylmethyl-4,5α-epoxy-8-hydrogen-3-hydroxy-morphinan-6-one, prior art compound TR-5118, exhibits mixed agonist side effects and antagonist properties. The 17-cyclobutyl-methyl-4,5α-epoxy-8-hydrogen-3-hydroxy-morphinan-6-one, reference compound TR-5128, exhibits so low an antagonist ability as to be ineffective in the practical sense. By contrast with the reference compound TR-5128 the 17-cyclobutylmethyl-4,5α-epoxy-3-hydroxy-8β-methylmorphinan-6-one compound of this invention unexpectedly possesses less side effects and dramatically increased antagonist properties.

What is claimed is:

1. 7,8 and 7-8 substituted 4,5α-epoxymorphinan-6-one compounds characterized by the structural formula:

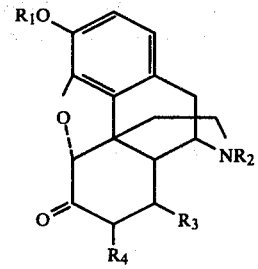

wherein $R_1$ is H or methyl; $R_2$ is cyclopropylmethyl, cyclobutylmethyl, allyl or tetrahydrofurfuryl; $R_3$ is β-methyl, β-ethyl or α-ethyl and $R_4$ is H or α-methyl, provided that:
   i. when $R_2$ is allyl, $R_3$ is β-ethyl, $R_4$ is H and $R_1$ is H;
   ii. when $R_2$ is tetrahydrofurfuryl, $R_3$ is β-ethyl, $R_4$ is H and $R_1$ is H;
   iii. when $R_2$ is cyclobutylmethyl, $R_1$ is H and $R_3$ and $R_4$ are, respectively, either β-ethyl and H, β-methyl and α-methyl or β-methyl and H;
   iv. when $R_2$ is cyclopropylmethyl and $R_1$ is methyl, $R_3$ is β-ethyl and $R_4$ is H; and
   v. when $R_2$ is cyclopropylmethyl and $R_1$ is H, $R_3$ and $R_4$ are, respectively, either β-ethyl and H, α-ethyl and H or β-methyl and α-methyl.

2. The compounds of claim 1 in the form of their pharmaceutically acceptable organic or inorganic acid addition salts.

3. A compound as defined by claim 1 wherein $R_1$ is methyl, $R_2$ is cyclopropylmethyl, $R_3$ is β-ethyl and $R_4$ is H.

4. The hydrochloric acid addition salt of the compound defined by claim 3.

5. A compound as defined by claim 1 wherein $R_1$ is H, $R_2$ is cyclopropylmethyl, $R_3$ is β-ethyl and $R_4$ is H.

6. A compound as defined by claim 1 wherein $R_1$ is H, $R_2$ is cyclobutylmethyl, $R_3$ is β-ethyl and $R_4$ is H.

7. The hydrochloric acid addition salt of the compound defined by claim 6.

8. A compound as defined by claim 1 wherein $R_1$ is H, $R_2$ is tetrahydrofurfuryl, $R_3$ is β-ethyl and $R_4$ is H.

9. The hydrochloric acid addition salt of the compound defined by claim 8.

10. A compound as defined by claim 1 wherein $R_1$ is H, $R_2$ is allyl, $R_3$ is β-ethyl and $R_4$ is H.

11. The hydrochloric acid addition salt of the compound defined by claim 10.

12. A compound as defined by claim 1 wherein $R_1$ is H, $R_2$ is cyclobutylmethyl, $R_3$ is β-methyl and $R_4$ is H.

13. The hydrochloric acid addition salt of the compound defined by claim 12.

14. A compound as defined by claim 1 wherein $R_1$ is H, $R_2$ is cyclopropylmethyl, $R_3$ is α-ethyl and $R_4$ is H.

15. The hydrochloric acid addition salt of the compound defined by claim 14.

16. A compound as defined by claim 1 wherein $R_1$ is H, $R_2$ is cyclopropylmethyl, $R_3$ is β-methyl and $R_4$ is α-methyl.

17. The hydrochloric acid addition salt of the compound defined by claim 16.

18. A compound as defined by claim 1 wherein $R_1$ is H, $R_2$ is cyclobutylmethyl, $R_3$ is β-methyl and $R_4$ is α-methyl.

19. A therapeutic method for treating pain in an individual for whom such therapy is indicated without liability of drug dependence which method comprises administering to the individual an analgesically effective amount of a compound characterized by the formula:

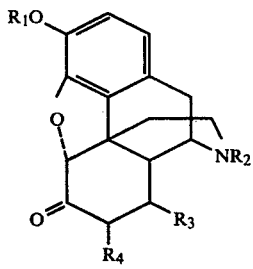

wherein $R_1$ is H or methyl; $R_2$ is cyclopropylmethyl, cyclobutylmethyl or tetrahydrofurfuryl; $R_3$ is β-methyl, β-ethyl or α-ethyl and $R_4$ is H or α-methyl, provided that:

i. when $R_2$ is tetrahydrofurfuryl, $R_3$ is β-ethyl, $R_4$ is H and $R_1$ is H;

ii. when $R_2$ is cyclobutylmethyl, $R_1$ is H and $R_3$ and $R_4$ are, respectively, either β-ethyl and H, β-methyl and α-methyl or β-methyl and H;

iii. when $R_2$ is cyclopropylmethyl and $R_1$ is methyl, $R_3$ is β-ethyl and $R_4$ is H; and iv. when $R_2$ is cyclopropylmethyl and $R_1$ is H, $R_3$ and $R_4$ are, respectively, either β-ethyl and H, or α-ethyl and H.

20. The method of claim 19 wherein the compound is administered in the form of its pharmaceutically acceptable organic or inorganic acid addition salt.

21. The method of claim 19 wherein the compound administered is further defined in that $R_1$ is methyl, $R_2$ is cyclopropylmethyl, $R_3$ is β-ethyl and $R_4$ is H.

22. The method of claim 21 wherein the compound is administered in the form of its hydrochloric acid addition salt.

23. The method of claim 19 wherein the compound administered is further defined in that $R_1$ is H, $R_2$ is cyclopropylmethyl, $R_3$ is β-ethyl and $R_4$ is H.

24. The method of claim 19 wherein the compound administered is further defined in that $R_1$ is H, $R_2$ is cyclobutylmethyl, $R_3$ is β-ethyl and $R_4$ is H.

25. The method of claim 24 wherein the compound is administered in the form of its hydrochloric acid addition salt.

26. The method of claim 19 wherein the compound administered is further defined in that $R_1$ is H, $R_2$ is tetrahydrofurfuryl, $R_3$ is β-ethyl and $R_4$ is H.

27. The method of claim 26 wherein the compound is administered in the form of its hydrochloric acid addition salt.

28. The method of claim 19 wherein the compound administered is further defined in that $R_1$ is H, $R_2$ is cyclobutylmethyl, $R_3$ is β-methyl and $R_4$ is H.

29. The method of claim 28 wherein the compound is administered in the form of its hydrochloric acid addition salt.

30. The method of claim 19 wherein the compound administered is further defined in that $R_1$ is H, $R_2$ is cyclopropylmethyl, $R_3$ is α-ethyl and $R_4$ is H.

31. The method of claim 30 wherein the compound is administered in the form of its hydrochloric acid addition salt.

32. The method of claim 19 wherein the compound administered is further defined in that $R_1$ is H, $R_2$ is cyclobutylmethyl, $R_3$ is β-methyl and $R_4$ is α-methyl.

33. A therapeutic method for treating drug dependence in an individual for whom such therapy is indicated, which method comprises administering to said individual an effective narcotic antagonist amount of a compound selected from the group of 17-allyl-4,5α-epoxy-8β-ethyl-3-hydroxymrophinan-6-one or 17-cyclopropylmethyl-4,5α-epoxy-3-hydroxy-7α-methyl-8β-methylmorphinan.

34. The method of claim 33 wherein the compound is administered in the form of its hydrochloric acid addition salt.

* * * * *